United States Patent
Raslambekov et al.

(10) Patent No.: US 11,600,376 B2
(45) Date of Patent: *Mar. 7, 2023

(54) SYSTEMS AND METHODS FOR GENERATING 3D-REPRESENTATION OF TOOTH-SPECIFIC PLATFORM FOR DENTAL APPLIANCE

(71) Applicant: Oxilio Ltd, Larnaca (CY)

(72) Inventors: Islam Khasanovich Raslambekov, Long Island City, NY (US); Khamzat Saidovich Asabaev, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 304 days.

This patent is subject to a terminal disclaimer.

(21) Appl. No.: 16/940,709

(22) Filed: Jul. 28, 2020

(65) Prior Publication Data
US 2021/0174935 A1  Jun. 10, 2021

Related U.S. Application Data

(63) Continuation of application No. 16/704,760, filed on Dec. 5, 2019, now Pat. No. 10,726,949.

(51) Int. Cl.
*G16H 30/20* (2018.01)
*G16H 70/20* (2018.01)

(52) U.S. Cl.
CPC ............. *G16H 30/20* (2018.01); *G16H 70/20* (2018.01)

(58) Field of Classification Search
CPC ........ G16H 30/20; G16H 70/20; A61C 7/002; A61C 7/12; A61C 7/14; A61C 7/145; A61C 7/16
See application file for complete search history.

(56) References Cited

U.S. PATENT DOCUMENTS

| 5,518,397 A | 5/1996 | Andreiko et al. |
| 5,975,893 A | 11/1999 | Chishti et al. |

(Continued)

FOREIGN PATENT DOCUMENTS

| CN | 107260337 A | 10/2017 |
| EP | 2881075 A1 | 6/2015 |

(Continued)

OTHER PUBLICATIONS

English Machine Translation of CN107260337A retrieved by the EPO on Apr. 27, 2021.

(Continued)

*Primary Examiner* — Jason B Dunham
*Assistant Examiner* — Christopher B Wehrly
(74) *Attorney, Agent, or Firm* — BCF LLP

(57) ABSTRACT

A method and processor for generating a 3D-platform representation of a tooth-specific platform for attachment of a dental appliance to a tooth of a patient are disclosed. The method includes acquiring a 3D-tooth representation of the tooth, and defining an attachment zone on the surface of the 3D-tooth representation. The attachment zone has a zone perimeter enclosing a surface portion of the 3D-tooth representation corresponding to a surface portion of the tooth to which the tooth-specific platform is to be attached. The method also includes generating the 3D-platform representation having (i) a tooth-oriented surface matching the surface portion of the 3D-tooth representation and having a perimeter matching the zone perimeter, (ii) a perimeter wall extending between the tooth-oriented surface and the tooth-opposite surface and away from the surface portion, and (iii) a tooth-opposite surface matching an expanded surface portion of the 3D-tooth representation.

18 Claims, 19 Drawing Sheets

(56) References Cited

U.S. PATENT DOCUMENTS

| | | |
|---|---|---|
| 6,044,954 A | 4/2000 | McLaughlin et al. |
| 6,183,248 B1 | 2/2001 | Chishti et al. |
| 6,227,850 B1 | 5/2001 | Chishti et al. |
| 6,309,215 B1 | 10/2001 | Phan et al. |
| 6,318,994 B1 | 11/2001 | Chishti et al. |
| 6,334,853 B1 | 1/2002 | Kopelman et al. |
| 6,386,878 B1 | 5/2002 | Pavlovskaia et al. |
| 6,398,548 B1 | 6/2002 | Muhammad et al. |
| 6,463,344 B1 | 10/2002 | Pavloskaia et al. |
| 6,471,511 B1 | 10/2002 | Chishti et al. |
| 6,554,611 B2 | 4/2003 | Chishti et al. |
| 6,602,070 B2 | 8/2003 | Miller et al. |
| 6,665,570 B2 | 12/2003 | Pavloskaia et al. |
| 6,685,470 B2 | 2/2004 | Chishti et al. |
| 6,688,886 B2 | 2/2004 | Hughes et al. |
| 6,705,863 B2 | 3/2004 | Phan et al. |
| 6,726,478 B1 | 4/2004 | Isiderio et al. |
| 6,739,870 B2 | 5/2004 | Lai et al. |
| 6,767,208 B2 | 7/2004 | Kaza |
| 6,979,196 B2 | 12/2005 | Nikolskiy et al. |
| 6,988,889 B2 | 1/2006 | Abels et al. |
| 7,040,896 B2 | 5/2006 | Pavlovskaia et al. |
| 7,059,850 B1 | 6/2006 | Phan et al. |
| 7,063,532 B1 | 6/2006 | Jones et al. |
| 7,123,767 B2 | 10/2006 | Jones et al. |
| 7,125,248 B2 | 10/2006 | Phan et al. |
| 7,134,874 B2 | 11/2006 | Chishti et al. |
| 7,220,122 B2 | 5/2007 | Chishti |
| 7,241,142 B2 | 7/2007 | Abolfathi et al. |
| 7,293,988 B2 | 11/2007 | Wen |
| 7,320,592 B2 | 1/2008 | Chishti et al. |
| 7,373,286 B2 | 5/2008 | Nikolskiy et al. |
| 7,377,778 B2 | 5/2008 | Chishti et al. |
| 7,428,481 B2 | 9/2008 | Nikolskiy et al. |
| 7,442,040 B2 | 10/2008 | Kuo |
| 7,637,740 B2 | 12/2009 | Knopp |
| 7,658,610 B2 | 2/2010 | Knopp |
| 7,689,398 B2 | 3/2010 | Cheng et al. |
| 7,771,195 B2 | 8/2010 | Knopp et al. |
| 7,826,646 B2 | 11/2010 | Pavlovskaia et al. |
| 7,841,858 B2 | 11/2010 | Knopp et al. |
| 7,844,429 B2 | 11/2010 | Matov et al. |
| 7,850,451 B2 | 12/2010 | Wiechmann et al. |
| 7,865,259 B2 | 1/2011 | Kuo et al. |
| 7,904,307 B2 | 3/2011 | Abolfathi et al. |
| 7,905,725 B2 | 3/2011 | Chishti et al. |
| 7,942,672 B2 | 5/2011 | Kuo |
| 7,993,134 B2 | 8/2011 | Wen |
| 8,038,444 B2 | 10/2011 | Kitching et al. |
| 8,108,189 B2 | 1/2012 | Chelnokov et al. |
| 8,131,393 B2 | 3/2012 | Matov et al. |
| 8,135,569 B2 | 3/2012 | Matov et al. |
| 8,244,390 B2 | 8/2012 | Kuo et al. |
| 8,371,847 B2 | 2/2013 | Baron et al. |
| 8,439,672 B2 | 5/2013 | Matov et al. |
| 8,465,280 B2 | 6/2013 | Sachdeva et al. |
| 8,478,435 B2 | 7/2013 | Kuo et al. |
| 8,562,339 B2 | 10/2013 | Raby |
| 8,639,477 B2 | 1/2014 | Chelnokov et al. |
| 8,641,414 B2 | 2/2014 | Borovinskih et al. |
| 8,694,142 B2 | 4/2014 | Yang et al. |
| 8,734,150 B2 | 5/2014 | Wen |
| 8,780,106 B2 | 7/2014 | Chishti et al. |
| 8,807,999 B2 | 8/2014 | Kuo et al. |
| 8,896,592 B2 | 11/2014 | Boltunov et al. |
| 8,897,902 B2 | 11/2014 | See et al. |
| 8,961,173 B2 | 2/2015 | Miller |
| 9,060,829 B2 | 6/2015 | Sterental et al. |
| 9,107,722 B2 | 8/2015 | Matov et al. |
| 9,161,823 B2 | 10/2015 | Morton et al. |
| 9,211,166 B2 | 12/2015 | Kuo et al. |
| 9,326,831 B2 | 5/2016 | Cheang |
| 9,345,557 B2 | 5/2016 | Anderson et al. |
| 9,375,293 B2 | 6/2016 | Taub et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,529,970 B2 | 12/2016 | Andreiko |
| 9,592,103 B2 | 3/2017 | Taub et al. |
| 9,610,140 B2 | 4/2017 | Anderson et al. |
| 9,622,834 B2 | 4/2017 | Chapoulaud et al. |
| 9,792,413 B2 | 10/2017 | Badawi |
| 9,844,424 B2 | 12/2017 | Wu et al. |
| 9,949,804 B2 | 4/2018 | Schlimper et al. |
| 10,011,050 B2 | 7/2018 | Kitching et al. |
| 10,076,389 B2 | 9/2018 | Wu et al. |
| 10,136,965 B2 | 11/2018 | Wiechmann et al. |
| 10,278,794 B1 | 5/2019 | Raslambekov |
| 10,307,222 B2 | 6/2019 | Morton et al. |
| 10,332,164 B2 | 6/2019 | Abolfathi et al. |
| 10,383,704 B2 | 8/2019 | Kitching |
| 10,405,947 B1 | 9/2019 | Kaza et al. |
| 10,405,951 B1 | 9/2019 | Kopelman et al. |
| 10,413,385 B2 | 9/2019 | Sherwood et al. |
| 10,433,934 B2 | 10/2019 | Kopelman |
| 10,463,452 B2 | 11/2019 | Matov et al. |
| 10,470,846 B2 | 11/2019 | Kopelman et al. |
| 10,524,880 B2 | 1/2020 | Wen |
| 10,553,309 B2 | 2/2020 | Trosien et al. |
| 10,561,476 B2 | 2/2020 | Matov et al. |
| 10,595,965 B2 | 3/2020 | Khardekar et al. |
| 10,617,489 B2 | 4/2020 | Grove et al. |
| 10,650,517 B2 | 5/2020 | Parpara et al. |
| 10,653,503 B2 | 5/2020 | Boltunov et al. |
| 10,783,629 B2 | 9/2020 | Parpara et al. |
| 10,792,127 B2 | 10/2020 | Kopelman et al. |
| 10,813,721 B2 | 10/2020 | Sterental et al. |
| 2005/0244791 A1 | 11/2005 | Davis et al. |
| 2007/0031774 A1 | 2/2007 | Cinader et al. |
| 2009/0017410 A1* | 1/2009 | Raby .............. A61C 7/146 433/2 |
| 2013/0095446 A1 | 4/2013 | Andreiko et al. |
| 2013/0125398 A1 | 5/2013 | Curiel et al. |
| 2014/0011154 A1 | 1/2014 | Curiel et al. |
| 2014/0288894 A1 | 9/2014 | Chishti et al. |
| 2014/0363782 A1* | 12/2014 | Wiechmann .......... A61C 7/20 433/9 |
| 2016/0228214 A1 | 8/2016 | Sachdeva et al. |
| 2016/0302885 A1 | 10/2016 | Matov et al. |
| 2017/0035536 A1 | 2/2017 | Alvarez Garcia et al. |
| 2017/0049534 A1 | 2/2017 | Soo et al. |
| 2017/0079748 A1 | 3/2017 | Andreiko |
| 2017/0135792 A1 | 5/2017 | Webber |
| 2017/0165032 A1 | 6/2017 | Webber et al. |
| 2017/0231721 A1 | 8/2017 | Akeel et al. |
| 2018/0039755 A1 | 2/2018 | Matov et al. |
| 2018/0165818 A1 | 6/2018 | Tsai et al. |
| 2018/0304497 A1 | 10/2018 | Kitching et al. |
| 2019/0000592 A1 | 1/2019 | Cam et al. |
| 2019/0046295 A1 | 2/2019 | Morton et al. |
| 2019/0282333 A1 | 9/2019 | Matov et al. |
| 2019/0314117 A1 | 10/2019 | Morton et al. |
| 2019/0357997 A1 | 11/2019 | Shi et al. |
| 2020/0000551 A1 | 1/2020 | Li et al. |
| 2020/0000552 A1 | 1/2020 | Mednikov et al. |
| 2020/0146776 A1 | 5/2020 | Matov et al. |
| 2020/0229900 A1 | 7/2020 | Cunliffe et al. |
| 2020/0297459 A1 | 9/2020 | Grove et al. |
| 2020/0306012 A1 | 10/2020 | Roschin et al. |

FOREIGN PATENT DOCUMENTS

| | | |
|---|---|---|
| WO | 98058596 A1 | 12/1998 |
| WO | 00019928 A1 | 4/2000 |
| WO | 00019930 A1 | 4/2000 |
| WO | 00019931 A1 | 4/2000 |
| WO | 00069356 A1 | 11/2000 |
| WO | 00069357 A1 | 11/2000 |
| WO | 01074268 A1 | 11/2001 |
| WO | 2001080761 A2 | 11/2001 |
| WO | 2018085718 A2 | 5/2018 |
| WO | 2018112073 A2 | 6/2018 |

(56) References Cited

FOREIGN PATENT DOCUMENTS

| WO | 2019089989 A2 | 5/2019 |
| WO | 2019155315 A1 | 8/2019 |

OTHER PUBLICATIONS

European Search Repod completed on Apr. 22, 2021 issued in respect of the counterpart EP Application No. 20212029.1.

* cited by examiner

SYSTEMS AND METHODS FOR GENERATING 3D-REPRESENTATION OF TOOTH-SPECIFIC PLATFORM FOR DENTAL APPLIANCE

CROSS-REFERENCE

The present application is a continuation of U.S. patent application Ser. No. 16/704,760 filed Dec. 5, 2019, the entirety of which is incorporated by reference.

FIELD

The present technology relates to dental appliances in general, and specifically, to methods and systems for generating a 3D-representation of a tooth-specific platform for a dental appliance.

BACKGROUND

In orthodontics, treatments for achieving alignment of malposed teeth in a patient include applying orthodontic appliances to the patient's teeth, such as pre-shaped orthodontic wire(s) attached to the brackets which are themselves attached to the teeth. The wires, also known as archwires, are typically made from shape memory alloys which have the ability to recover their shape after being deformed. This re-shaping occurs at a predetermined temperature, usually around 38° C. Shape memory alloys used in orthodontic archwires include nickel-titanium alloys (e.g. Nitinol™), beta-titanium alloys, and copper nickel-titanium alloys.

The wires are typically pre-shaped into a desired shape by forming bends at desired positions and with desired angles, heating under tension, and super-cooling. The heating step typically comprises electric heating. Once pre-shaped, the wire is attached to the brackets by bending its shape to conform to the general shape of the malposed teeth. When the wire warms to mouth temperature it reverts to its original shape thereby exerting a force on the teeth to which it is attached to move them.

A typical orthodontic treatment comprises a number of consecutive treatment steps in which wires of different shapes and/or stiffness may be used for applying different forces to the teeth as the alignment progresses. In some cases, the treatment steps may be classified as an aligning stage, a levelling stage, a working stage, a finishing stage and a settling stage. In some cases, the treatment stages comprise an initial stage, a transitional stage and a finishing stage. The treatment stages may include an imposed orthodontic action such as rotation or linear movement of one or more teeth, development of the arch form, a levelling of the arches, torque control or simple retention of the position. Generally, the earlier treatment stages apply more gentle forces compared to the main treatment stages. Thicker wires may be used for the more aggressive repositioning phase.

As a result, it is important for the archwire to be securely attached to the teeth of a patient during each treatment stage of the orthodontic treatment plan.

SUMMARY

It is an object of the present technology to ameliorate at least some of the inconveniences present in the prior art.

It is contemplated that at least some embodiments of the present technology may be beneficial for lingual and/or labial treatments of a patient. Some embodiments of the present technology provide customizable dental appliances, such as tooth-specific platforms and tooth-specific brackets for example. As it will become apparent from the disclosure herein, at least some embodiments of the present technology may allow a skilled professional to design and/or manufacture platforms and brackets that are customized to the specific needs of a tooth during the treatment plan.

Tooth-specific platforms and brackets designed and/or manufactured as disclosed herein may also allow reduction of their thickness which may lead to several advantages as compared to prior art systems. It is contemplated that at least some embodiments of the present technology may allow decreasing articulation problems, decreasing tongue irritation during the treatment, decreasing risk of bracket breakage and/or loss. Also, it is contemplated that some embodiments of the present technology may allow reduction of distance between an archwire of an orthodontic appliance and the teeth of the patient. As a result, a more accurate movement of teeth throughout a treatment plan due to the closer proximity of the archwire to the teeth. In addition, other embodiments of the present technology, may allow increasing the comfort of the patient during the treatment as well as an increase oral hygiene conditions of the patent.

At least some non-limiting embodiments of the tooth-specific platforms and brackets may have better fixation properties compared to standard braces. This is achieved at least partially due to the fact that the platform is configured to repeat the contour of the tooth it is designed for.

In at least some non-limiting embodiments of the present technology, tooth-specific brackets have lower profile of the bracket, therefore, greater comfort of wearing in the mouth for the patient. In at least some non-limiting embodiments of the present technology, adaptation of the wings contributes to the reduction of the profile of the bracket, and due to the controlled gap between the wing and the platform, the non-limiting embodiments of the present technology may ensure that there is sufficient space for the installation of ligatures.

In a first broad aspect of the present technology, there is provided a method of generating a 3D-platform representation of a tooth-specific platform for a dental appliance for use with a tooth of a patient. The tooth-specific platform is for attachment of the dental appliance to the tooth. The method is executable by a processor. The method comprises acquiring, by the processor, a 3D-tooth representation of the tooth. the 3D-tooth representation has a surface and has been generated based on the tooth of the patient. The method comprises defining, by the processor, an attachment zone on the surface of the 3D-tooth representation. The attachment zone has a zone perimeter enclosing a surface portion of the 3D-tooth representation which corresponds to a surface portion of the tooth to which the tooth-specific platform is to be attached. The method comprises generating, by the processor, the 3D-platform representation having (i) a tooth-oriented surface, (ii) a perimeter wall, and (iii) a tooth-opposite surface. The generating the 3D-platform representation includes projecting, by the processor, a print object onto the surface of the 3D-tooth representation, and thereby defining a projected object matching at least a portion of the surface of the 3D-tooth representation. The generating the 3D-platform representation includes using, by the processor, the zone perimeter for cutting the projected object, and thereby defining a tooth-oriented surface of the 3D-platform representation. The tooth-oriented surface matches the surface portion of the 3D-tooth representation and has a perimeter matching the zone perimeter. The generating the 3D-platform representation includes extruding, by the processor, the tooth-oriented surface into a pre-determined direction, and thereby defining a preliminary 3D-platform representation that has (i) the tooth-oriented surface, (ii) a preliminary perimeter wall, and (iii) another surface. The generating the 3D-platform representation includes expanding, by the processor, the 3D-tooth representation by a pre-determined distance, and thereby generating an expanded 3D-tooth representation having an expanded surface. The generating the 3D-platform representation includes using, by the processor, the expanded surface for cutting the preliminary 3D-platform representation along the preliminary perimeter wall, and thereby defining (i) the perimeter wall and (ii) the tooth-opposite surface of the 3D-platform representation. The perimeter wall extends(i) between the tooth-oriented surface and the tooth-opposite surface and (ii) away from the surface portion. The tooth-opposite surface matches an expanded surface portion of the 3D-tooth representation.

In some embodiments of the method, the dental appliance is a bracket.

In some embodiments of the method, the bracket is a tooth-specific bracket.

In a second broad aspect of the present technology, there is provided a method of generating a 3D-platform representation of a tooth-specific platform for attachment of a dental appliance to a tooth of a patient. The method is executable by a processor. The method comprises acquiring, by the processor, a 3D-tooth representation of the tooth. The 3D-tooth representation has a surface and has been generated based on the tooth of the patient. The method comprises defining, by the processor, an attachment zone on the surface of the 3D-tooth representation. The attachment zone has a zone perimeter enclosing a surface portion of the 3D-tooth representation which corresponds to a surface portion of the tooth to which the tooth-specific platform is to be attached. The method comprises generating, by the processor, the 3D-platform representation having (i) a tooth-oriented surface, (ii) a perimeter wall, and (iii) a tooth-opposite surface. The tooth-oriented surface matches the surface portion of the 3D-tooth representation and has a perimeter matching the zone perimeter. The perimeter wall extends (i) between the tooth-oriented surface and the tooth-opposite surface and (ii) away from the surface portion. The tooth-opposite surface matches an expanded surface portion of the 3D-tooth representation.

In some embodiments of the method, the dental appliance is a bracket.

In some embodiments of the method, the bracket is a tooth-specific bracket.

In some embodiments of the method, the expanded surface portion does not match the surface portion.

In some embodiments of the method, the defining the attachment zone comprises defining, by the processor, an attachment point on the surface of the 3D-tooth representation. The defining the attachment zone also comprises using, by the processor, the attachment point for defining the zone perimeter of the attachment zone. The attachment point is enclosed by the zone perimeter of the attachment zone.

In some embodiments of the method, the using the attachment point for defining the zone perimeter of the attachment zone comprises determining, by the processor, a minimum area for attaching the tooth-specific platform on the tooth. The using the attachment point for defining the zone perimeter of the attachment zone also comprises defining, by the processor, the zone perimeter of the attachment zone around the attachment point such that the zone perimeter encloses the surface portion having at least the minimum area.

In some embodiments of the method, the generating the 3D-platform representation comprises generating, by the processor, a preliminary 3D-platform representation, and generating, by the processor, the 3D-platform representation from the preliminary 3D-platform representation.

In some embodiments of the method, the generating the preliminary 3D-platform representation comprises projecting, by the processor, a print object onto the surface of the 3D-tooth representation, and thereby defining a projected object matching at least a portion of the surface of the 3D-tooth representation. The generating the preliminary 3D-platform representation also comprises using, by the processor, the zone perimeter for cutting the projected object, and thereby defining the tooth-oriented surface of the 3D-platform representation. The tooth-oriented surface matches the surface portion of the 3D-tooth representation and has a perimeter that matches the zone perimeter. The generating the preliminary 3D-platform representation also comprises extruding, by the processor, the tooth-oriented surface into a pre-determined direction, and thereby defining the preliminary 3D-platform representation that has (i) the tooth-oriented surface, (ii) a preliminary perimeter wall, and (iii) another surface.

In some embodiments of the method, the print object has a grid-type relief.

In some embodiments of the method, the generating the 3D-platform representation from the preliminary 3D-platform representation comprises expanding, by the processor, the 3D-tooth representation by a pre-determined distance, and thereby generating an expanded 3D-tooth representation having an expanded surface. The generating the 3D-platform representation from the preliminary 3D-platform representation comprises using, by the processor, the expanded surface for cutting the preliminary 3D-platform representation along the preliminary perimeter wall, and thereby defining (i) the perimeter wall and (ii) the tooth-opposite surface of the 3D-platform representation.

In some embodiments of the method, the method further comprises triggering, by the processor, manufacture of the tooth-specific platform based on the 3D-platform representation.

In some embodiments of the method, the manufacture is performed by an additive manufacturing technique.

In some embodiments of the method, the manufacture is performed by a melting technique.

In some embodiments of the method, the method further comprises generating, by the processor, a 3D-bracket representation of a bracket to be to be attached to the tooth. The bracket is the dental appliance.

In some embodiments of the method, the method further comprises triggering, by the processor, manufacture of the tooth-specific platform and of the bracket based on the 3D-platform representation and on the 3D-bracket representation.

In some embodiments of the method, the tooth-specific platform and the bracket are integrally fabricated.

In some embodiments of the method, the tooth-specific platform and the bracket are integrally fabricated by an additive manufacturing technique.

In a third broad aspect of the present technology, there is provided a processor for generating a 3D-platform representation of a tooth-specific platform for a dental appliance for use with a tooth of a patient. The tooth-specific platform is for attachment of the dental appliance to the tooth. The processor is configured to acquire a 3D-tooth representation of the tooth. The 3D-tooth representation has a surface and has been generated based on the tooth of the patient. The processor is configured to define an attachment zone on the surface of the 3D-tooth representation. The attachment zone has a zone perimeter enclosing a surface portion of the 3D-tooth representation which corresponds to a surface portion of the tooth to which the tooth-specific platform is to be attached. The processor is configured to generate the 3D-platform representation having (i) a tooth-oriented surface, (ii) a perimeter wall, and (iii) a tooth-opposite surface. The processor configured to generate includes the processor configured to project a print object onto the surface of the 3D-tooth representation, and thereby defining a projected print object matching at least a portion of the surface of the 3D-tooth representation. The processor configured to generate includes the processor configured to use the zone perimeter for cutting the projected print object, and thereby defining a tooth-oriented surface of the 3D-platform representation. The tooth-oriented surface matches the surface portion of the 3D-tooth representation and has a perimeter matching the zone perimeter. The processor configured to generate includes the processor configured to extrude the tooth-oriented surface into a pre-determined direction, and thereby defining a preliminary 3D-platform representation having (i) the tooth-oriented surface, (ii) a preliminary perimeter wall, and (iii) another surface. The processor configured to generate includes the processor configured to expand the 3D-tooth representation by a pre-determined distance, and thereby generating an expanded 3D-tooth representation having an expanded surface. The processor configured to generate includes the processor configured to use the expanded surface for cutting the preliminary 3D-platform representation along the preliminary perimeter wall, and thereby defining (i) the perimeter wall and (ii) the tooth-opposite surface of the 3D-platform representation. The perimeter wall extends (i) between the tooth-oriented surface and the tooth-opposite surface and (ii) away from the surface portion. The tooth-opposite surface matches an expanded surface portion of the 3D-tooth representation.

In some embodiments of the processor, the dental appliance is a bracket.

In some embodiments of the processor, the bracket is a tooth-specific bracket.

In a fourth broad aspect of the present technology, there is provided a processor for generating a 3D-platform representation of a tooth-specific platform for attachment of a dental appliance to a tooth of a patient. The processor is configured to acquire a 3D-tooth representation of the tooth. The 3D-tooth representation has a surface and has been generated based on the tooth of the patient. The processor is configured to define an attachment zone on the surface of the 3D-tooth representation. The attachment zone has a zone perimeter enclosing a surface portion of the 3D-tooth representation which corresponds to a surface portion of the tooth to which the tooth-specific platform is to be attached. The processor is configured to generate the 3D-platform representation having (i) a tooth-oriented surface, (ii) a perimeter wall, and (iii) a tooth-opposite surface. The tooth-oriented surface matches the surface portion of the 3D-tooth representation and has a perimeter matching the zone perimeter. The perimeter wall extends (i) between the tooth-oriented surface and the tooth-opposite surface and (ii) away from the surface portion. The tooth-opposite surface matches an expanded surface portion of the 3D-tooth representation.

In some embodiments of the processor, the dental appliance is a bracket.

In some embodiments of the processor, the bracket is a tooth-specific bracket.

In some embodiments of the processor, the expanded surface portion does not match the surface portion.

In some embodiments of the processor, the processor configured to define the attachment zone comprises the processor is configured to (i) define an attachment point on the surface of the 3D-tooth representation, and (ii) use the attachment point for defining the zone perimeter of the attachment zone. The attachment point is enclosed by the zone perimeter of the attachment zone.

In some embodiments of the processor, the processor configured to use the attachment point for defining the zone perimeter of the attachment zone comprises the processor being configured to (i) determine a minimum area for attaching the tooth-specific platform on the tooth, and (ii) define the zone perimeter of the attachment zone around the attachment point such that the zone perimeter encloses the surface portion having at least the minimum area.

In some embodiments of the processor, the processor configured to generate the 3D-platform representation comprises the processor being configured to (i) generate a preliminary 3D-platform representation, and (ii) generate the 3D-platform representation from the preliminary 3D-platform representation.

In some embodiments of the processor, the processor configured to generate the preliminary 3D-platform representation comprises the processor configured to project a print object onto the surface of the 3D-tooth representation, and thereby defining a projected print object matching at least a portion of the surface of the 3D-tooth representation. The processor configured to generate the preliminary 3D-platform representation comprises the processor configured to use the zone perimeter for cutting the projected print object, and thereby defining the tooth-oriented surface of the 3D-platform representation. The tooth-oriented surface matches the surface portion of the 3D-tooth representation and has a perimeter matching the zone perimeter. The processor configured to generate the preliminary 3D-platform representation comprises the processor configured to extrude the tooth-oriented surface into a pre-determined direction, and thereby defining the preliminary 3D-platform representation that has (i) the tooth-oriented surface, (ii) a preliminary perimeter wall, and (iii) another surface.

In some embodiments of the processor, the print object has a grid-type relief.

In some embodiments of the processor, the processor configured to generate the 3D-platform representation from the preliminary 3D-platform representation comprises the processor being configured to (i) expand the 3D-tooth representation by a pre-determined distance, and thereby generating an expanded 3D-tooth representation having an expanded surface, and (ii) use the expanded surface for cutting the preliminary 3D-platform representation along the preliminary perimeter wall, and thereby defining the perimeter wall and the tooth-opposite surface of the 3D-platform representation.

In some embodiments of the processor, the processor is further configured to trigger manufacture of the tooth-specific platform based on the 3D-platform representation.

In some embodiments of the processor, the manufacture is performed by an additive manufacturing technique.

In some embodiments of the processor, the manufacture is performed by a melting technique.

In some embodiments of the processor, the processor is further configured to generate a 3D-bracket representation of a bracket to be to be attached to the tooth. The bracket is the dental appliance.

In some embodiments of the processor, the processor is further configured to trigger manufacture of the tooth-specific platform and of the bracket based on the 3D-platform representation and on the 3D-bracket representation.

In some embodiments of the processor, the tooth-specific platform and the bracket are integrally fabricated.

In some embodiments of the processor, the tooth-specific platform and the bracket are integrally fabricated by an additive manufacturing technique.

In a fifth broad aspect of the present technology, there is provided a method of generating a 3D representation of a tooth-specific dental appliance for use with a tooth of a patient. The tooth-specific appliance is for attachment to the tooth. The tooth-specific appliance has a grooved body and a pair of holding arms. The method is executable by a processor. The method comprises acquiring, by the processor, a 3D-platform representation of a platform. The tooth-specific dental appliance is to be attached to the tooth via the platform. The method comprises acquiring, by the processor, a 3D-grooved body representation of the grooved body. The grooved body is to be attached to the platform. The method comprises positioning, by the processor, the 3D-grooved body representation relative to the 3D-platform representation, and thereby defining a position of the 3D-grooved body representation which corresponds to a position of attachment of the tooth-specific appliance on the platform. The method comprises acquiring, by the processor, a first 3D-arm representation of a first holding arm and a second 3D-arm representation of a second holding arm. Each one of the first and the second 3D-arm representations has (i) a respective pair of platform anchor points and (ii) a respective adjustment anchor point. The method comprises individually positioning, by the processor, the first 3D-arm representation and the second 3D-arm representation relative to the 3D-platform representation using the respective pairs of platform anchor points, and thereby defining (i) a preliminary position of the first 3D-arm representation and (ii) a preliminary position of the second 3D-arm representation. The method comprises individually adjusting, by the processor, the respective preliminary position of the first 3D-arm representation and of the second 3D-arm representation relative to the 3D-grooved body representation using the respective adjustment anchor points, and thereby defining an adjusted position of the first 3D-arm representation and an adjusted position of the second 3D-arm representation. The adjusted positions of the first and the second 3D-arm representations and the position of the 3D-grooved body representation correspond to a position of the tooth-specific appliance relative to the platform when attached to the platform.

In some embodiments of the method, the individually positioning the first and the second 3D-arm representations comprises: (i) positioning, by the processor, the first 3D-arm representation relative to the 3D-platform representation using the respective pair of platform anchor points, and (ii) positioning, by the processor, the second 3D-arm representation relative to the 3D-platform representation using the respective pair of platform anchor points. The positioning the first 3D-arm representation is performed by the processor independently from the positioning the second 3D-arm representation.

In some embodiments of the method, the individually adjusting the respective preliminary positions of the first 3D-arm representation and of the second 3D-arm representation comprises (i) adjusting, by the processor, the preliminary position of the first 3D-arm representation relative to the 3D-grooved body representation using the respective adjustment anchor point, and (ii) adjusting, by the processor, the preliminary position of the second 3D-arm representation relative to the 3D-grooved body representation using the respective adjustment anchor point. The adjusting the preliminary position of the first 3D-arm representation is performed by the processor independently from the adjusting the preliminary position of the second 3D-arm representation.

In some embodiments of the method, the individually positioning the first and the second 3D-arm representations is performed by the processor independently from the positioning the 3D-grooved body representation.

The method of claim 1, wherein the individually positioning the first and the second 3D-arm representations comprises (i) positioning, by the processor, the first 3D-arm representation relative to the 3D-platform representation using the respective pair of platform anchor points, and (ii) positioning, by the processor the second 3D-arm representation relative to the 3D-platform representation using the respective pair of platform anchor points. The positioning the second 3D-arm representation being performed after the positioning of the first 3D arm representation.

In some embodiments of the method, the individually positioning the first and the second 3D-arm representations is performed after the positioning the 3D-grooved body representation relative to the 3D-platform representation.

In some embodiments of the method, the acquiring the 3D-grooved body representation is performed by the processor independently from the acquiring the 3D-arm representations.

In some embodiments of the method, the 3D-platform representation has a first attachment point and the 3D-grooved body representation has a second attachment point. The positioning the 3D-grooved body representation comprises positioning, by the processor, the 3D-grooved body representation relative to the 3D-platform representation such that the first attachment point and the second attachment point coincide.

In some embodiments of the method, the acquiring the 3D-grooved body representation of the grooved body comprises: (i) acquiring, by the processor, a 3D-groove structure representation corresponding to a pre-determined groove shape in the grooved body, (ii) acquiring, by the processor, a 3D-body structure representation corresponding to a pre-determined body shape of the grooved body, and (iii) performing, by the processor, a boolean operation between the 3D-groove structure representation and the 3D-body structure representation, and thereby defining the 3D-grooved body representation.

In some embodiments of the method, at least one of (i) the 3D-grooved body representation of the grooved body, (ii) the first 3D-arm representation, and (iii) the first 3D-arm representation, is pre-stored in a library communicatively coupled to the processor.

In some embodiments of the method, the at least two of the at least one of (i) the 3D-grooved body representation of the grooved body, (ii) the first 3D-arm representation, and (iii) the first 3D-arm representation, are individually acquired by the processor from the library.

In some embodiments of the method, the method further comprises triggering, by the processor, manufacture of the tooth-specific dental appliance based on at least in part the 3D representation of the tooth-specific appliance.

In some embodiments of the method, the tooth-specific appliance is a tooth-specific bracket.

In a sixth broad aspect of the present technology, there is provided a processor for generating a 3D representation of a tooth-specific dental appliance for use with a tooth of a patient. The tooth-specific appliance is for attachment to the tooth. The tooth-specific appliance has a grooved body and a pair of holding arms. The processor is configured to acquire a 3D-platform representation of a platform. The tooth-specific dental appliance is to be attached to the tooth via the platform. The processor is configured to acquire a 3D-grooved body representation of the grooved body. The grooved body is to be attached to the platform. The processor is configured to position the 3D-grooved body representation relative to the 3D-platform representation, and thereby defining a position of the 3D-grooved body representation corresponding to a position of attachment of the tooth-specific appliance on the platform. The processor is configured to acquire a first 3D-arm representation of a first holding arm and a second 3D-arm representation of a second holding arm. Each one of the first and the second 3D-arm representations has (i) a respective pair of platform anchor points and (ii) a respective adjustment anchor point. The processor is configured to individually position the first 3D-arm representation and the second 3D-arm representation relative to the 3D-platform representation using the respective pairs of platform anchor points, and thereby defining (i) a preliminary position of the first 3D-arm representation and (ii) a preliminary position of the second 3D-arm representation. The processor is configured to individually adjust the respective preliminary position of the first 3D-arm representation and of the second 3D-arm representation relative to the 3D-grooved body representation using the respective adjustment anchor points, and thereby defining an adjusted position of the first 3D-arm representation and an adjusted position of the second 3D-arm representation. The adjusted positions of the first and the second 3D-arm representations and the position of the 3D-grooved body representation corresponding to a position of the tooth-specific appliance relative to the platform when attached to the platform.

In some embodiments of the processor, the processor is configured to trigger manufacture of the tooth-specific dental appliance based on at least in part the 3D-bracket representation.

In some embodiments of the processor, the processor configured to individually position the first and the second 3D-arm representations comprises the processor configured to (i) position the first 3D-arm representation relative to the 3D-platform representation using the respective pair of platform anchor points, and (ii) position the second 3D-arm representation relative to the 3D-platform representation using the respective pair of platform anchor points. The positioning the first 3D-arm representation is performed by the processor independently from the positioning the second 3D-arm representation.

In some embodiments of the processor, the processor configured to individually adjust the respective preliminary positions of the first 3D-arm representation and of the second 3D-arm representation comprises the processor configured to (i) adjust the preliminary position of the first 3D-arm representation relative to the 3D-grooved body representation using the respective adjustment anchor point, and (ii) adjust the preliminary position of the second 3D-arm representation relative to the 3D-grooved body representation using the respective adjustment anchor point. The adjusting the preliminary position of the first 3D-arm representation is performed by the processor independently from the adjusting the preliminary position of the second 3D-arm representation.

In some embodiments of the processor, the processor is configured to individually position the first and the second 3D-arm representations independently from the positioning the 3D-grooved body representation.

In some embodiments of the processor, the processor configured to individually position the first and the second 3D-arm representations comprises the processor being configured to (i) position the first 3D-arm representation relative to the 3D-platform representation using the respective pair of platform anchor points, and (ii) position the second 3D-arm representation relative to the 3D-platform representation using the respective pair of platform anchor points. The positioning the second 3D-arm representation is performed after the positioning of the first 3D arm representation.

In some embodiments of the processor, the processor is configured to individually position the first and the second 3D-arm representations after the positioning the 3D-grooved body representation relative to the 3D-platform representation.

In some embodiments of the processor, the processor is configured to acquire the 3D-grooved body representation independently from the acquiring the 3D-arm representations.

In some embodiments of the processor, the 3D-platform representation has a first attachment point and the 3D-grooved body representation has a second attachment point. The processor configured to position the 3D-grooved body representation comprises the processor configured to position the 3D-grooved body representation relative to the 3D-platform representation such that the first attachment point and the second attachment point coincide.

In some embodiments of the processor, the processor configured to acquire the 3D-grooved body representation of the grooved body comprises the processor configured to (i) acquire a 3D-groove structure representation corresponding to a pre-determined groove shape in the grooved body, (ii) acquire a 3D-body structure representation corresponding to a pre-determined body shape of the grooved body, and (iii) perform a boolean operation between the 3D-groove structure representation and the 3D-body structure representation, and thereby defining the 3D-grooved body representation.

In some embodiments of the processor, at least one of (i) the 3D-grooved body representation of the grooved body, (ii) the first 3D-arm representation, and (iii) the first 3D-arm representation, is pre-stored in a library communicatively coupled to the processor.

In some embodiments of the processor, the at least two of the at least one of (i) the 3D-grooved body representation of the grooved body, (ii) the first 3D-arm representation, and (iii) the first 3D-arm representation, are individually acquired by the processor from the library.

In some embodiments of the processor, the processor is further configured to trigger manufacture of the tooth-specific dental appliance based on at least in part the 3D representation of the tooth-specific appliance.

In some embodiments of the processor, the tooth-specific appliance is a tooth-specific bracket.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

Figure 1:
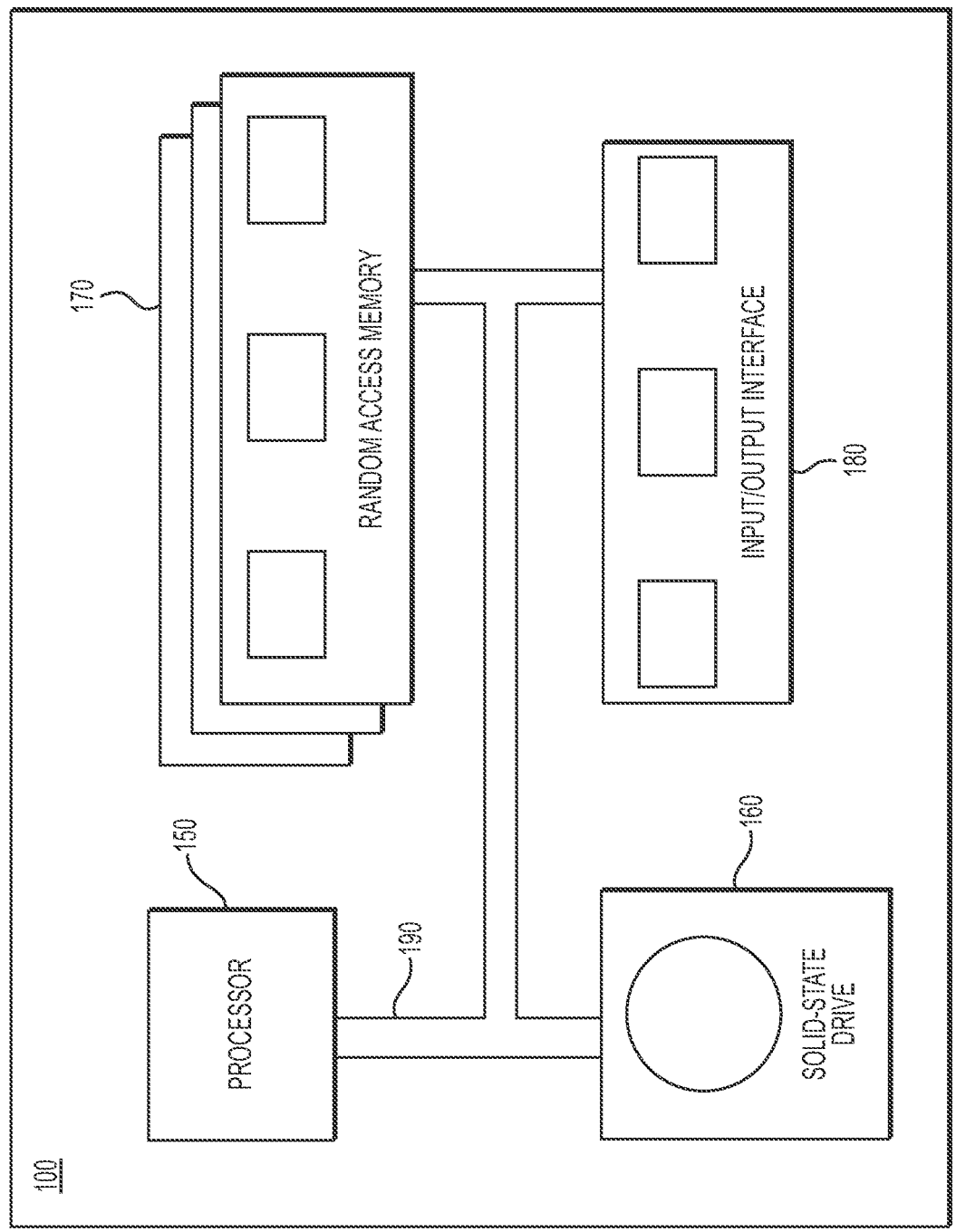
FIG. 1 depicts a computer environment as implemented in accordance with at least some non-limiting embodiments of the present technology.

It should be noted that, unless otherwise explicitly specified herein, the drawings are not to scale.

DETAILED DESCRIPTION

The examples and conditional language recited herein are principally intended to aid the reader in understanding the principles of the present technology and not to limit its scope to such specifically recited examples and conditions. It will be appreciated that those skilled in the art may devise various arrangements which, although not explicitly described or shown herein, nonetheless embody the principles of the present technology and are included within its spirit and scope.

Furthermore, as an aid to understanding, the following description may describe relatively simplified implementations of the present technology. As persons skilled in the art would understand, various implementations of the present technology may be of a greater complexity.

In some cases, what are believed to be helpful examples of modifications to the present technology may also be set forth. This is done merely as an aid to understanding, and, again, not to define the scope or set forth the bounds of the present technology. These modifications are not an exhaustive list, and a person skilled in the art may make other modifications while nonetheless remaining within the scope of the present technology. Further, where no examples of modifications have been set forth, it should not be interpreted that no modifications are possible and/or that what is described is the sole manner of implementing that element of the present technology.

Moreover, all statements herein reciting principles, aspects, and implementations of the technology, as well as specific examples thereof, are intended to encompass both structural and functional equivalents thereof, whether they are currently known or developed in the future. Thus, for example, it will be appreciated by those skilled in the art that any block diagrams herein represent conceptual views of illustrative circuitry embodying the principles of the present technology. Similarly, it will be appreciated that any flowcharts, flow diagrams, state transition diagrams, pseudocode, and the like represent various processes which may be substantially represented in computer-readable media and so executed by a computer or processor, whether or not such computer or processor is explicitly shown.

The functions of the various elements shown in the figures, including any functional block labeled as a "processor", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read-only memory (ROM) for storing software, random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown.

With these fundamentals in place, we will now consider some non-limiting examples to illustrate various implementations of aspects of the present technology.

Computer Environment

With reference FIG. 1, there is depicted a non-limiting example of a computer environment 100 as contemplated in at least some embodiments of the present technology. As seen, the computer environment 100 comprises various hardware components including, but not limited to: one or more single or multi-core processors collectively represented by a processor 150, a solid-state drive 160, a random access memory 170 and an input/output interface 180. Communication between the various components of the computer environment 100 may be enabled by one or more internal and/or external buses 190 (e.g. a PCI bus, universal serial bus, IEEE 1394 "Firewire" bus, SCSI bus, Serial-ATA bus, ARINC bus, etc.), to which the various hardware components are electronically coupled.

How the processor 150 is implemented is not particularly limited. However, broadly speaking, the processor 150 may be implemented as an electronic circuit configured to perform operations (e.g., processing) on some data provided thereto from a local and/or remote source, and typically, from a memory or some other data stream.

How the solid-state drive 160 is implemented is not particularly limited. However, broadly speaking, the solid-state drive 160 may be implemented as a solid-state storage device that uses integrated circuit assemblies as memory to persistently store data. Nevertheless, it is contemplated that other media used as memory to persistently store data, without departing from the scope of the present technology.

How the random access memory 170 is implemented is not particularly limiting. However, broadly speaking, the random access memory 170 may be implemented as a form of computer data storage that stores data and/or machine code (e.g., computer-readable instructions) that is currently being used by the computer environment 100.

In accordance with at least some implementations of the computer environment 100, the solid-state drive 160 may be configured to store program instructions suitable for being loaded into the random access memory 170 and executed by the processor 150. For example, the program instructions may be part of a library and/or an application that the computer environment 100 is configured to execute. In another example, as it will become apparent from the description herein below, the program instructions may be part of a software dedicated for designing 3D representations of objects to be manufactured, which program instructions the computer environment 100 may be configured to execute.

How the input/output interface 180 is implemented is not particularly limiting. However, broadly speaking, the input/output interface 180 may be implemented so as to allow enabling networking capabilities, such as wire or wireless access, for example. As an example, the input/output interface 180 comprises a networking interface such as, but not limited to, a network port, a network socket, a network interface controller and the like. Multiple examples of how the networking interface may be implemented will become apparent to the person skilled in the art of the present technology.

For example, but without being limiting, the networking interface may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

The computer environment 100 may be implemented as part of a generic computer system such as, for example, a conventional computer (i.e. an "off the shelf" generic computer system). The generic computer system may a desktop computer/personal computer, but may also be any other type of electronic device such as, but not limited to, a laptop, a mobile device, a smart phone, a tablet device, or a server.

In other embodiments, the computer environment 100 is implemented in a device specifically dedicated to the implementation of the present technology. For example, the computer environment 100 is implemented in an electronic device such as, but not limited to, a desktop computer/personal computer, a laptop, a mobile device, a smart phone, a tablet device, a server, specifically designed for inter alia determining an orthodontic treatment plan, designing orthodontic appliance(s) for various treatment stages, enabling manufacture of at least some components of an orthodontic appliance, and the like. The electronic device may also be dedicated to operating other devices (such as imaging device and/or an manufacturing apparatus, which will be discussed in greater detail below with reference to FIG. 2) without departing from the scope of the present technology.

Computer System

Figure 2:
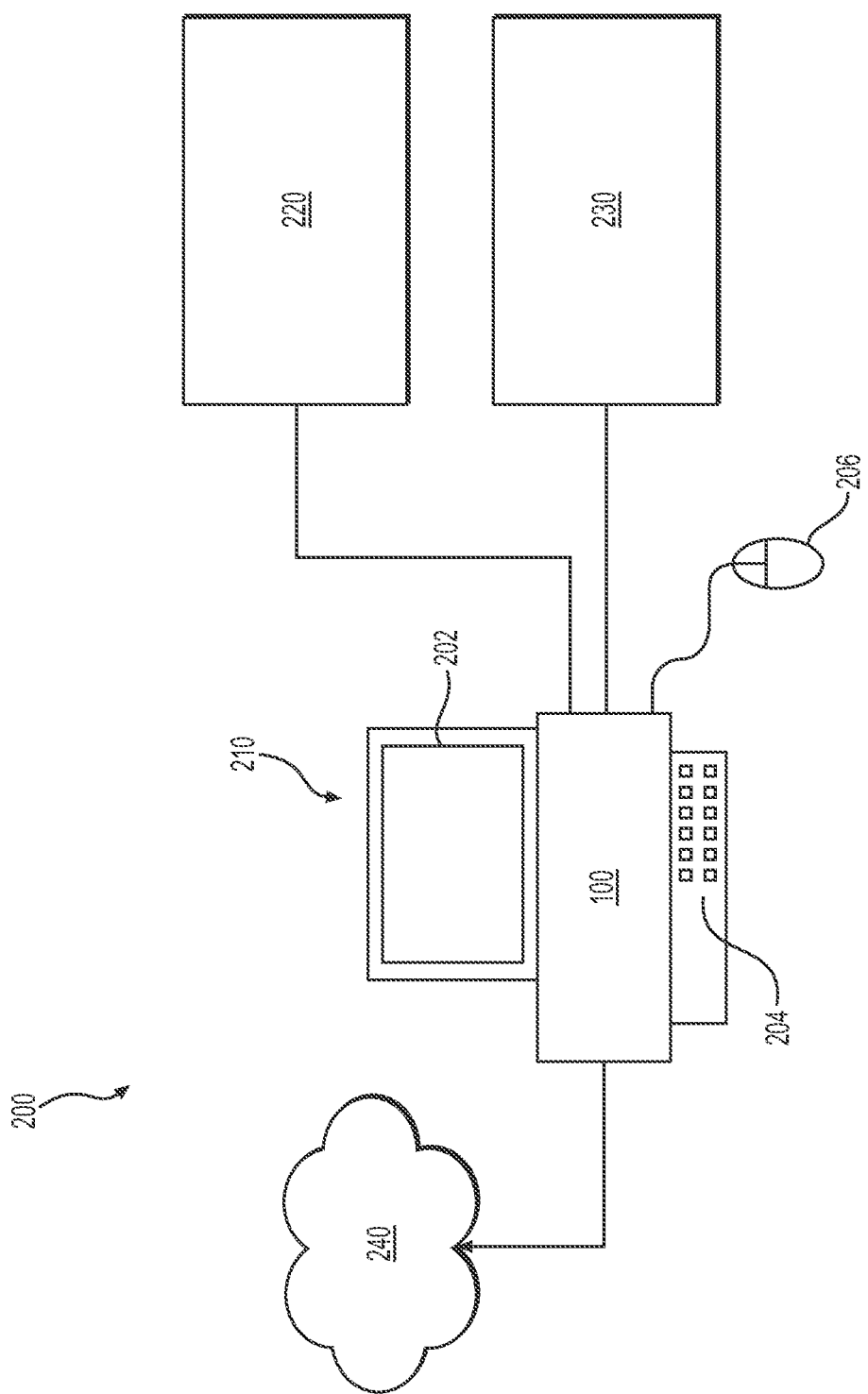
FIG. 2 depicts a computer system as implemented in accordance with at least some non-limiting embodiments of the present technology.

With reference to FIG. 2, there is depicted a non-limiting example of a computer system 200 as contemplated in at least some embodiments of the present technology. Broadly speaking, the computer system 200 is configured to inter alia (i) process information associated with a patient, (ii) generate 3D representations of at least some components of an orthodontic appliance based on that information, and (iii) manufacture (and/or generate instructions for triggering manufacture of) the at least some components of the orthodontic appliance based on the respective 3D representations.

As it will be described in greater detail herein further below, the computer system 200 may be configured to acquire and process information representative of at least a portion of an oral region of the patient. For example, the computer system 200 may be configured to process this information for allowing a user/operator of the computer system 200 to design at least some components of an orthodontic appliance such as, for example, tooth-specific dental appliances (e.g., tooth-specific brackets, tooth-specific platforms, and the like) for attachment of the tooth-specific dental appliances to respective teeth of the patient.

However, in other embodiments of the present technology, the computer system 200 may be configured to process the information representative of at least a portion of an oral region of the patient for designing at least some components of an orthodontic appliance with minimal or no operator intervention (e.g., with little or no direct operator control). Put another way, the computer system 200 may be configured to design at least some components of an orthodontic appliance in an automatic or semi-automatic manner, without departing from the scope of the present technology. For example, to that end, in at least some embodiments of the present technology, the computer system 200 may be configured to employ computer-readable instructions (such as software, for example) for auto-generating at least some components of the orthodontic appliance.

As it will also be described in greater detail herein further below, the computer system 200 may be configured to manufacture (and/or generate data indicative of instructions for manufacturing) at least some components of the orthodontic appliance. For example, the computer system 200 may be configured to (i) process information indicative the at least some components of the orthodontic appliance as designed by the operator and/or auto-generated by the computer system 200 and (ii) manufacture (and/or provide instructions for manufacturing) these components in a variety of ways.

However, in other embodiments of the present technology, the computer system 200 may be configured to manufacture (and/or generate data indicative of instructions for manufacturing) the at least some components of the orthodontic appliance with minimal or no operator intervention (e.g., with little or no direct operator control). Put another way, the computer system 200 may be configured to manufacture (and/or generate data indicative of instructions for manufacturing) the at least some components of the orthodontic appliance in an automatic or semi-automatic manner, without departing from the scope of the present technology. For example, to that end, in at least some embodiments of the present technology, the computer system 200 may be configured to employ computer-readable instructions (such as software, for example) for auto-manufacturing (and/or generating data indicative of instructions for auto-manufacturing) the at least some components of an orthodontic appliance.

In summary, it is contemplated that in at least some embodiments of the present technology, the computer system 200 may or may not require operator input or interaction for generating 3D representations of at least some dental appliances and for manufacturing (and/or generating data indicative of instructions for manufacturing) the at least some dental appliances.

In at least some embodiments of the present technology, the computer system 200 may comprise (i) an interface device 210, (ii) an imaging device 220, (iii) a manufacturing apparatus 230, and (iv) a communication network 240, which will now be discussed in turn.

Interface Device

Broadly speaking, the interface device 210 of the computer system 200 is configured for receiving inputs and/or providing outputs to the operator of the computer system 200. For example, the interface device 210 may include a display 202 (such as a screen, for example) for providing a visual output to the operator of the computer system 200.

The interface device 201 may also comprise a keyboard 204 and/or a mouse 206 for receiving inputs from the operator of the computer system 200.

In some embodiments, the interface device 210 may be configured to implement the computer environment 100 of FIG. 1 for processing inputs and/or outputs for the operator of the computer system 200. Put another way, the interface device 210 of the computer system 200 may comprise some or all components of the computer environment 100, without departing from the scope of the present technology.

In some embodiments of the present technology, the interface device 210 implementing the computer environment 100 may be configured to execute software programs and/or applications for the purpose of aiding the operator of the computer system 200 during design of at least some components of the orthodontic appliance.

For instance, the interface device 210 may be configured to execute Computer-Aided Design (CAD) software. Broadly speaking, CAD software is typically used for increasing the productivity of the operator during the design process, improving the quality of the design itself, and generating digital models for manufacturing purposes. For instance, when executed by the interface device 210, the CAD software may be used by the operator of the computer system 200 for inter alia importing/exporting 3D models, designing curves, surfaces, and/or solids in a 3D virtual environment, and the like.

It is contemplated that the interface device 210 may be configured to execute any 3D graphics software that aids the operator of the computer system 200 during design of the at least some components of the orthodontic appliance.

In other embodiments of the present technology, the interface device 210 implementing the computer environment 100 may be configured to execute software programs and/or applications for the purpose of generating 3D representations of the at least some components of the orthodontic appliance in an automatic and/or semi-automatic manner (e.g., with little or no intervention of the operator).

For instance, such software programs and/or applications may be configured to acquire information representative of at least a portion of the oral region of the patient and, based on that information, automatically and/or semi-automatically generate 3D representations of the at least some components of the orthodontic appliance. In at least some embodiments of the present technology, such software programs and/or applications may be employed by the computer system 200 for execution of at least some computer-implemented methods disclosed herein.

Imaging Device

As mentioned above, the computer system 200 also comprises the imaging device 220. Broadly speaking, the imaging device 220 may be implemented as any imaging device that is configured to capture and/or process images of a patient's mouth. In some embodiments, it is contemplated that the imaging device 220 may be configured to capture and/or process images of teeth and/or surrounding tissues of the patient's mouth. For instance, the information representative of at least a portion of the oral region of the patient may be composed, at least partially, of the images captured and/or processed by the imaging device 220 (for example, see FIG. 3).

In some embodiments, the images captured and/or processed by the imaging device 220 may include, but are not limited to: images of crown portions of teeth (internal and/or external), images of root portions of teeth (internal and/or external), images of tissues surrounding the teeth, images of nerve pathways in the teeth and/or in the surrounding tissues, images of bones such as jaw bones, other images of the oral region, and the like.

It should be noted that images captured and/or processed by the imaging device 220 may be in 2D and/or 3D. For example, the images captured and/or processed by the imaging device 220 may be, but are not limited to: computed tomography (CT) images, x-ray images, digitalized 3D physical model images, magnetic resonance images, nuclear medicine images, photographic images, and the like. Any type of image format visualizing the tooth and/or the surrounding areas may be potentially acceptable within the context of the present technology.

In some embodiments of the present technology, the imaging device 220 may be implemented as an intra-oral scanner for providing 3D digital models of the teeth of the patient (e.g., 3D representations of the teeth of the patient). Typically, intra-oral scanners have a component that (i) can be received in the oral region, (ii) has a light source for providing light to the oral region requiring imaging, and (iii) has an imaging sensor for capturing images of the oral region. It is contemplated that the intra-oral scanner may comprise an internal computer system that can (i) receive the captured images and (ii) generate digital 3D surface models (for example, in a "mesh" form) of the oral region. This technique provides an alternative to making traditional plaster models of the oral region followed by their digital imaging.

In other embodiments of the present technology, the imaging device 220 may be implemented as a Computed Tomography (CT) scanner for providing CT scan images. Typically, CT scan images are 3D images and provide x-ray level detail of the teeth, soft tissues, nerve pathways and bone. Optionally, other types of CT scanners can be used to provide panoramic, cephalometric or cone beam projections, without departing from the scope of the present technology.

In further embodiments of the present technology, the imaging device 220 may be implemented as any one of or any combination of: an x-ray apparatus for providing x-ray 2D images of the oral region, a magnetic resonance imaging device for providing magnetic resonance images, an ultrasound apparatus for providing ultrasound images of the oral region, and the like. Irrespective of the particular implementation of the imaging device 220, it is contemplated that the imaging device 220 may comprise at least one hardware processor for processing the images and at least one memory component for storing the images.

Manufacturing Apparatus

As mentioned above, the computer system 200 also comprises the manufacturing apparatus 230. Broadly speaking, the manufacturing apparatus 230 comprises any manufacturing apparatus that may be configured to manufacture at least some components of orthodontic appliances. For instance, the manufacturing apparatus 230 may be configured to inter alia (i) acquire data indicative of instructions for manufacturing the at least some components of the orthodontic appliance, and (ii) execute those instructions for manufacturing the at least some components of the orthodontic appliance.

The manufacturing apparatus 230 may be configured to manufacture a variety of components of the orthodontic appliance such as, but not limited to: platforms, brackets, archwires, trainers, retainers, mouth-guards, and/or any other type of dental appliance.

In some embodiments, where the manufacturing apparatus 230 is configured to manufacture platforms and/or brackets, the manufacturing apparatus 230 may include, but is not limited to: a casting apparatus, a moulding apparatus, an additive manufacturing apparatus (e.g., 3D printing apparatus), a melting apparatus, and the like.

In other embodiments, where the manufacturing apparatus 230 is configured to manufacture archwires, the manufacturing apparatus 230 may include, but is not limited to: a robotic bending apparatus, a heating/cooling apparatus, a smart material manufacturing apparatus, and the like.

In further embodiments, where the manufacturing apparatus 230 is configured to manufacture trainers, retainers and/or mouth-guards, the manufacturing apparatus 230 may include, but is not limited to: a thermoforming apparatus, a moulding apparatus, an additive manufacturing apparatus (e.g., 3D printing apparatus), and the like.

It is contemplated that the computer system 200 may also include a combination of various types of manufacturing apparatuses for manufacturing a various types of components of the orthodontic appliance, without departing from the scope of the present technology.

Communication Network

As mentioned above, the computer system 200 also comprises the communication network 240. In some embodiments of the present technology, the communication network 240 is the Internet. In alternative non-limiting embodiments, the communication network can be implemented as any suitable local area network (LAN), wide area network (WAN), a private communication network or the like. It should be expressly understood that implementations for the communication network are for illustration purposes only. A communication link (not separately numbered) between the interface device 210 and the communication network 240 is implemented will depend inter alia on how the interface device 210 is implemented. Merely as an example and not as a limitation, in those embodiments of the present technology where the interface device 210 is implemented as a wireless communication device such as a smartphone or a tablet, the communication link can be implemented as a wireless communication link. Examples of wireless communication links include, but are not limited to, a 3G communication network link, a 4G communication network link, and the like.

In some embodiments of the present technology, the communication network 240 may allow the computer system 200 to provide and/or acquire information from external/remote computer systems. For example, the communication network 240 may communicatively couple the computer system 200 with computer systems of other operators and/or of other entities, such as orthodontic clinics.

3D Image

Figure 3:
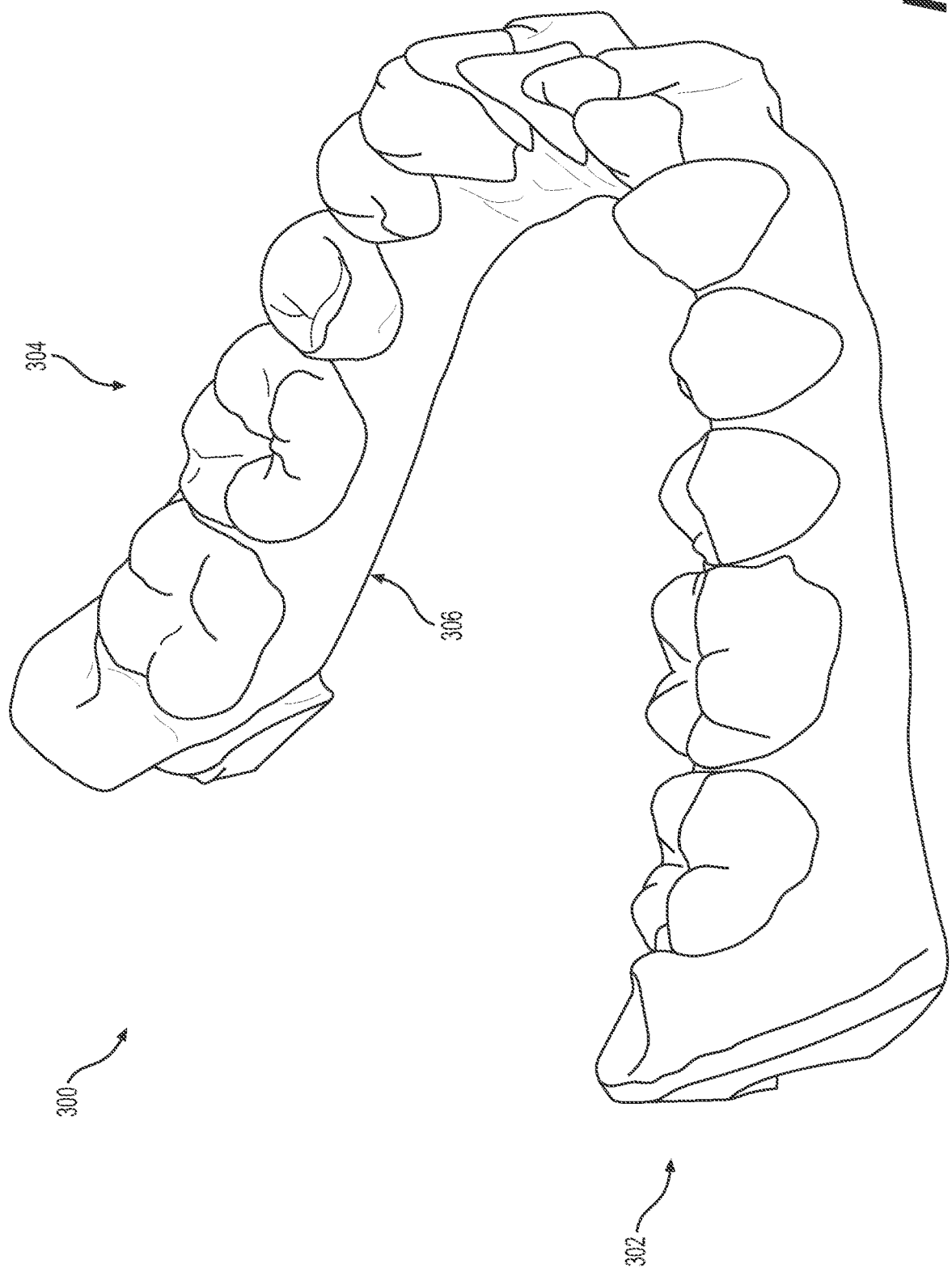
FIG. 3 is a schematic illustration of a 3D-arch representation of a dental arch of a patient generated by an imaging device of the computer system of FIG. 2, in accordance with at least some non-limiting embodiments of the present technology.

With reference to FIG. 3, there is depicted a 3D image 300 of at least a portion of an oral region of a patient. For instance, the 3D image 300 generally shows a lower jaw 302 of the patient. The 3D image 300 also shows a plurality of crown portions of teeth located on the lower jaw 302, including a crown portion 304, and surrounding tissues 306 of the teeth located on the lower jaw 302.

As mentioned above, it is contemplated that the 3D image 300 may be captured by the imaging device 220 implemented as the intra-oral scanner. The format in which the 3D image 300 is generated by the imaging device 220 and/or acquired by the computer system 200 is not particularly limited. However, just as an example, the 3D image 300 may be generated by the imaging device 220 and/or acquired by the computer system 200 in STL format and/or OBJ format.

In the context of the present technology, it is contemplated that the 3D image 300 is a 3D representation of the at least the portion of the oral region of the patient. It can thus be said that the 3D image 300 is a 3D object representative of the at least the portion of the oral region of the patient.

Orthodontic Appliance

As previously alluded to, the computer system 200 may be configured to aid the operator to design at least some components of an orthodontic appliance and/or generate automatically and/or semi-automatically the at least some components of an orthodontic appliance.

Figure 4:
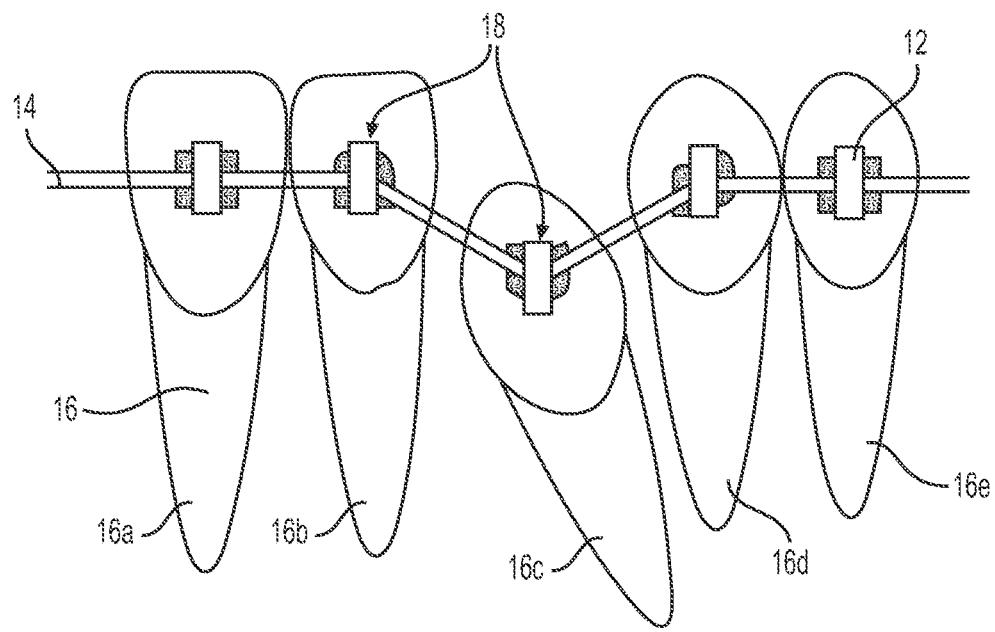
FIG. 4 is a schematic illustration of an orthodontic appliance attached to five teeth of a plurality of teeth of a patient and manufactured by an orthodontic manufacturing apparatus of the computer system of FIG. 2, in accordance with at least some non-limiting embodiments of the present technology.
Figure 5:
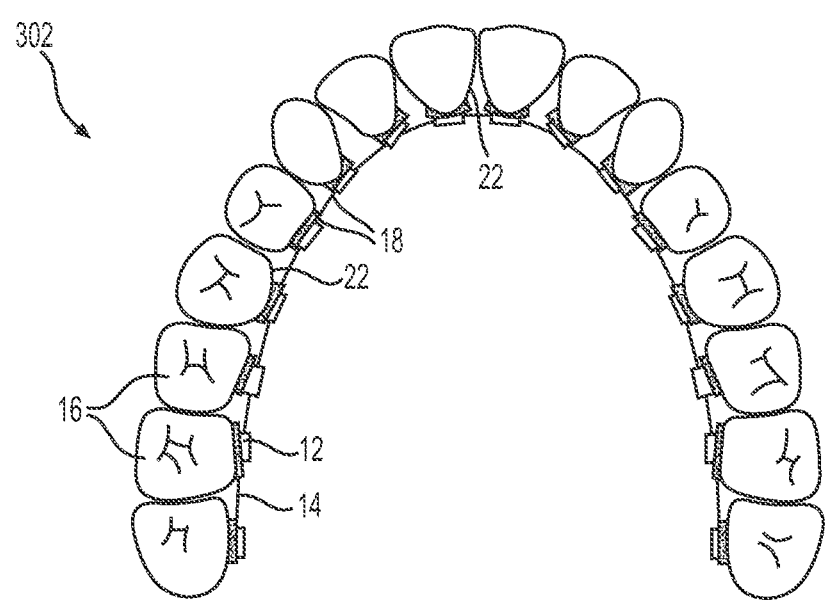
FIG. 5 is a schematic illustration of the entire lower archform of the patient showing the orthodontic appliance of FIG. 4 attached thereto.

With reference to FIGS. 4 and 5, there is depicted an example of an orthodontic appliance 10, the at least some components of which may be designed and/or manufactured using the computer system 200. The orthodontic appliance 10 comprises (i) an archwire 14, (ii) tooth-specific dental appliances, such as tooth-specific brackets 12, and (iii) other tooth-specific dental appliances, such as tooth-specific platforms 18.

For instance, the archwire 14 may be made of a shape memory alloy such as Nitinol™, but can also be made of any other shape memory alloy or material with elastic properties. The tooth-specific brackets 12 are provided on respective teeth 16 (shown individually as 16a, 16b, 16c, 16d, 16e), and the archwire 14 extends between, and is connected to, each of the tooth-specific brackets 12. In this example, the patient has a malocclusion—that is, a misalignment of the tooth 16c for which the treatment plan includes an upward movement of the tooth 16c so that the tooth 16c is aligned with neighboring the teeth 16a, 16b, 16d, 16e.

FIG. 5 depicts the orthodontic appliance 10 applied to all the teeth 16 of the lower jaw 302, with the tooth-specific brackets 12 being attached to internal surfaces 22 of the teeth 16 via respective tooth-specific platforms 18. In this example, the orthodontic appliance 10 is applied in a lingual configuration (attached to inner-sides of the teeth 16 of the lower jaw 302). However, it is contemplated that the orthodontic appliance 10 may be applied in other configurations, such as in a buccal configuration (attached to outer-sides of the teeth 16 of the lower jaw 302) for example.

It is also contemplated that in other embodiments of the present technology, the orthodontic appliance 10 may be applied on teeth of an upper jaw of the patient in any one of a palatal configuration (attached to inner-sides of teeth of the upper jaw) and a labial configuration (attached to outer-sides of the teeth of the upper jaw).

It should also be noted that the present technology can be applied to different types, shapes, sizes and configurations of orthodontic appliances 10 such as, without limitation, multi-strand wires, strips, retainers, and plates. It will also be appreciated that the orthodontic appliance 10 may be used for treating any type of teeth misalignment or malocclusion, including but not limited to closing gaps ("space closure"), creating/widening gaps, tooth rotation, tooth intrusion/extrusion, and translation, to name a few.

Tooth-Specific Dental Appliances

Figure 6:
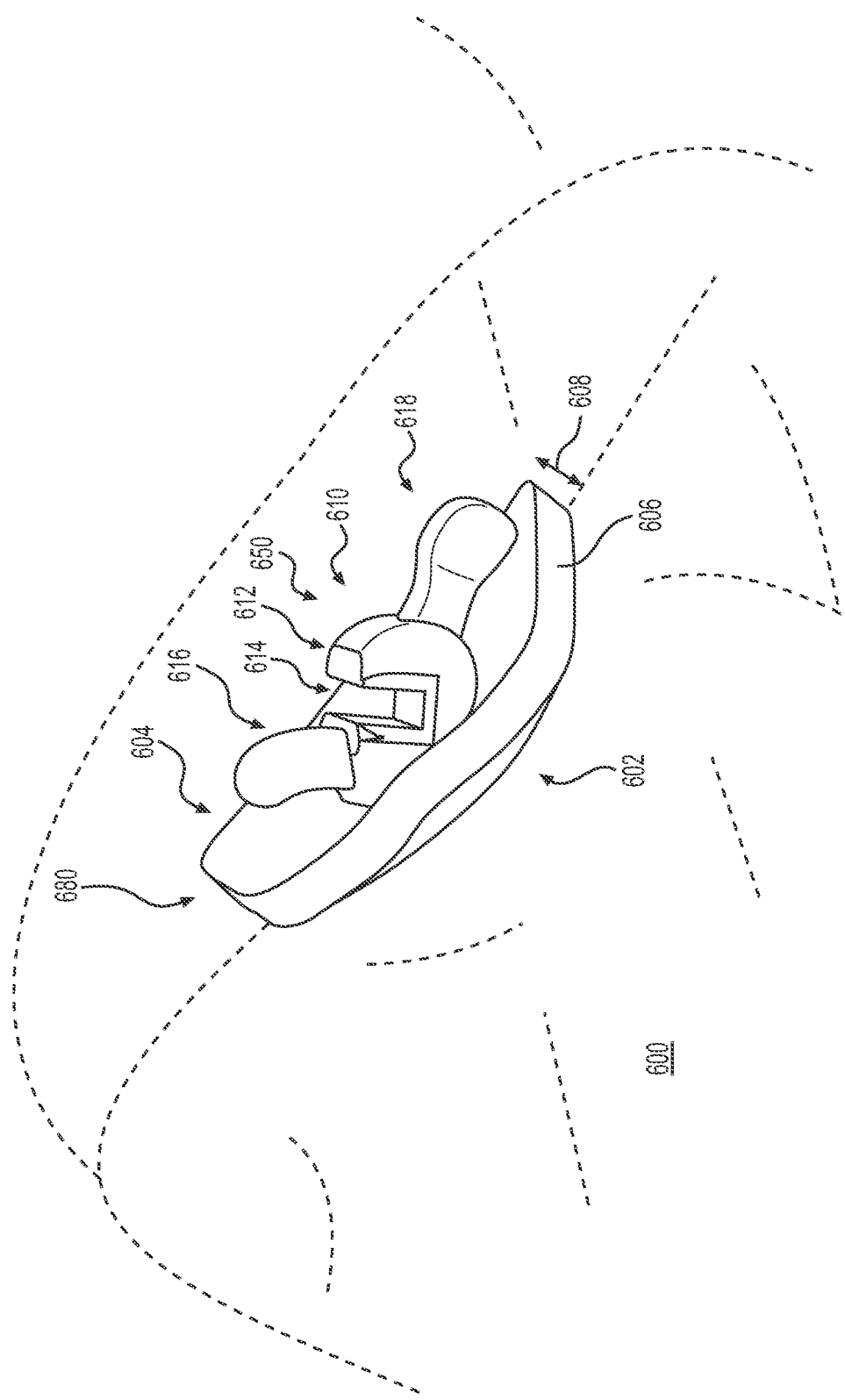
FIG. 6 is a schematic illustration of a tooth-specific bracket attached to a tooth-specific platform attached to a tooth of the patient (which has been dotted out).

With reference to FIG. 6, there is depicted a zoomed-in view of a tooth-specific appliance, such as a tooth-specific bracket 650, attached via a tooth-specific platform 680 to a respective tooth 600 which is depicted in dashed lines for ease of illustration. For example, the tooth-specific bracket 650 may be attached via the tooth-specific platform 680 to the respective tooth 600 similarly to how the tooth-specific bracket 12 is attached via the tooth-specific platform 18 to the respective tooth 16 in FIG. 5.

Broadly speaking, the tooth-specific platform 680 has (i) a tooth-oriented surface 602, (ii) a tooth-opposite surface 604, and (iii) a perimeter wall 606 with a thickness 608. The tooth-oriented surface 602 is generally used to attach the tooth-specific platform 680 to the respective tooth 600. The tooth-opposite surface 604 is generally used to attach the tooth-specific bracket 650 to the tooth-specific platform 680, and as a result, to the respective tooth 600.

In the context of the present technology, the tooth-specific platform 680 is said to be "tooth-specific" in the sense that it may be designed and/or manufactured specifically for the respective tooth 600—that is, the tooth-oriented surface 602 of the tooth-specific platform 680 may be designed and/or manufactured based on a shape of the respective tooth 600. How the tooth-specific platform 680 and, more particularly, how the tooth-oriented surface 602, the tooth-opposite surface 604, and the perimeter wall 606 may be designed by the computer system 200 will be discussed in greater details herein further below.

Broadly speaking, the tooth-specific bracket 650 has (i) a grooved body 610, composed of a body structure 612 in which a groove 614 is defined, and (ii) a pair of holding arms, namely a first holding arm 616 and a second holding arm 618. The grooved body 610 is used to attach the tooth-specific bracket 650 to the tooth-opposite surface 604 of the tooth-specific platform 680, thereby attaching the tooth-specific bracket 650 to the respective tooth 600 via the tooth-specific platform 680. The grooved body 610 is also used to receive the archwire 14 (see FIG. 5) into the groove 614 defined in the body structure 612.

As for the pair of holding arms, the first holding arm 616 and the second holding arm 618 are used for securing the archwire 14 inside the groove 614 by means of a securing element, such as an elastic band for example. For instance, one side of the elastic band may be inserted between the first holding arm 616 and the tooth-opposite surface 604 of the tooth-specific platform 680, and the other side of the elastic band may be inserted between the second holding arm 618 and the tooth-opposite surface 604 of the tooth-specific platform 680, such that it is stretched over the grooved body 610 and the archwire 14 so as to secure the archwire 14 inside the groove 614.

In the context of the present technology, the tooth-specific bracket 650 is said to be a "tooth-specific" dental appliance in the sense that it may be designed and/or manufactured specifically for the respective tooth 600—that is, a position on the tooth-specific platform 680, a form, and/or a configuration of the tooth-specific bracket 650 may be designed based on a desired state of the respective tooth 600 in the treatment plan of the patient. How the tooth-specific bracket 650 and, more particularly, how the grooved body 610, the first holding arm 616 and the second holding arm 618 may be designed and/or manufactured by the computer system 200 will be discussed in greater details herein further below.

As previously alluded to, the computer system 200 may be used for (i) designing (e.g., generating 3D representations of) the tooth-specific platform 680 and/or the tooth-specific bracket 650 and (ii) manufacturing (and/or generating instructions for manufacturing) the tooth-specific platform 680 and/or the tooth-specific bracket 650. Put another way, in at least some embodiments of the present technology, the computer system 200 may be configured to (i) generate a given 3D representation of the tooth-specific platform 680 and/or the tooth-specific bracket 650, and (ii) manufacture (and/or generating instructions for manufacturing) the tooth-specific platform 680 and/or the tooth-specific bracket 650 based on the given 3D representation.

How the computer system 200 is configured to generate the 3D representation of the tooth-specific platform 680 and the 3D representation of the tooth-specific bracket 650 will now be discussed in turn.

Design Process of the Tooth-Specific Platform

A process of designing of a given tooth-specific platform will now be discussed with reference to FIGS. 7 to 16. More particularly, how the computer system 200 is configured to generate a 3D-platform representation 1600 (see FIG. 16) corresponding to the given tooth-specific platform will now be discussed.

Figure 7:
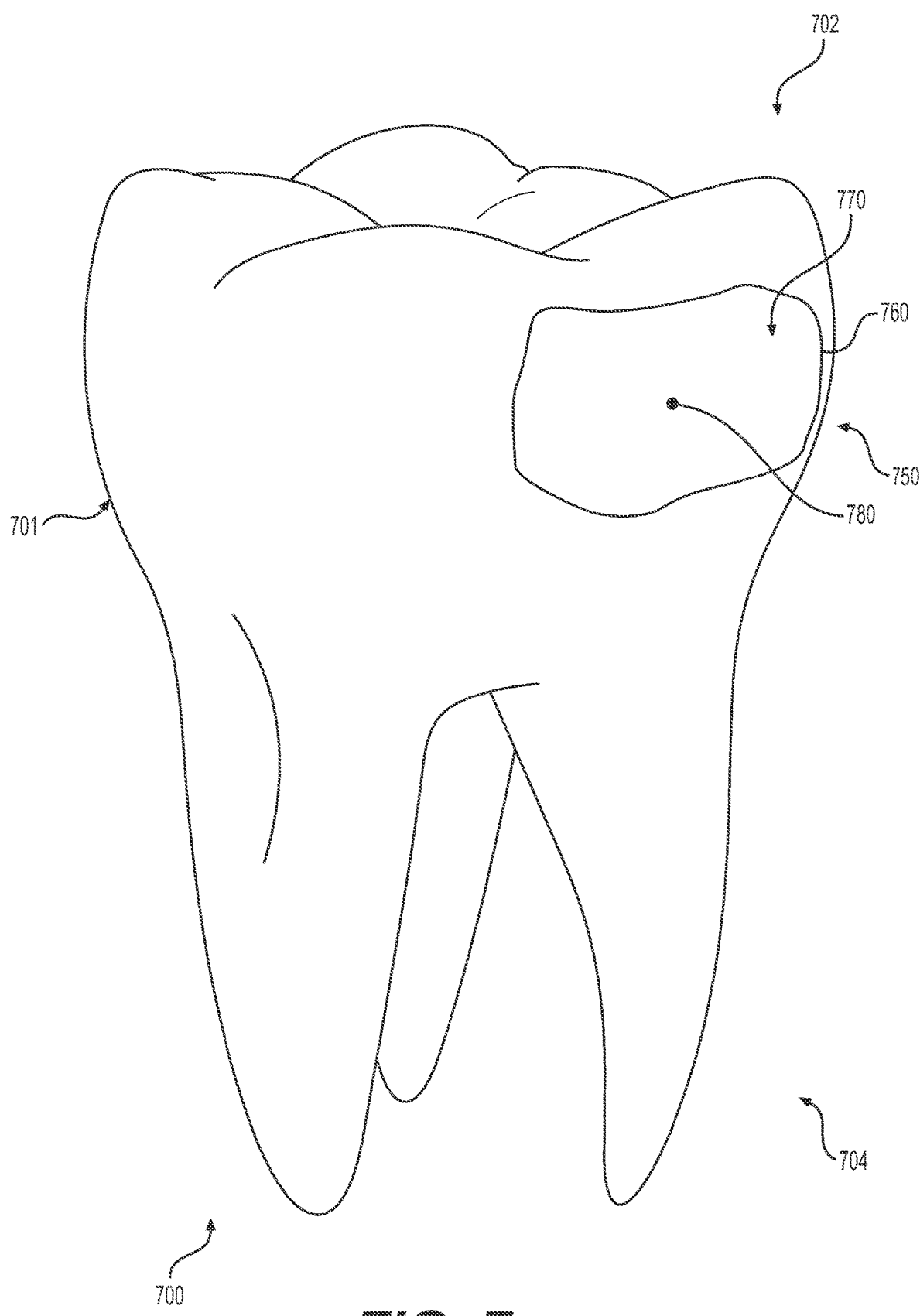
FIG. 7 is a schematic illustration of a 3D-tooth representation of a specific tooth of the patient and of a zone perimeter of an attachment zone of a surface of the 3D-tooth representation, in accordance with at least some embodiments of the present technology.
Figure 9:
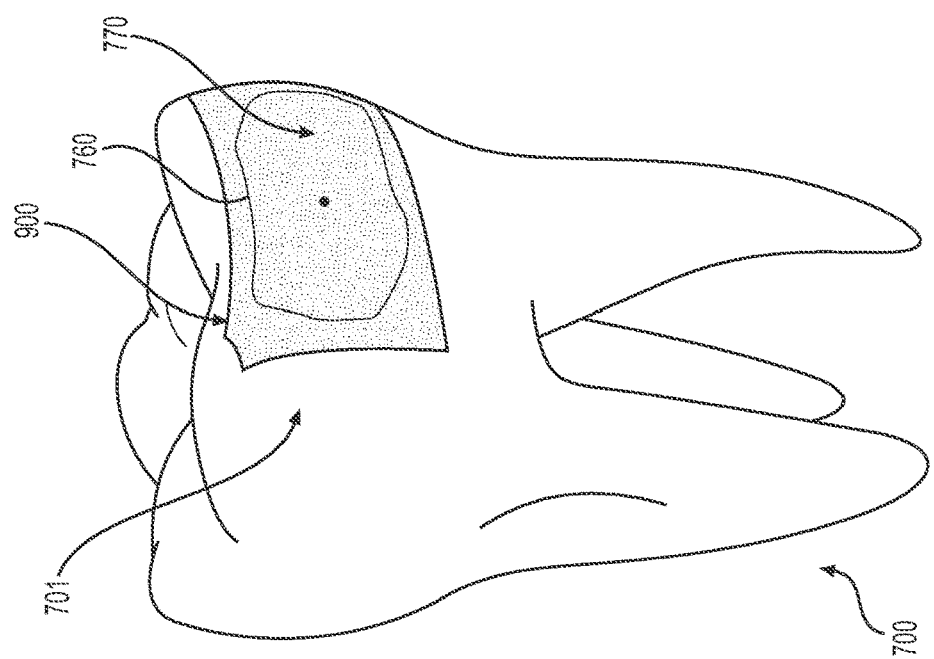
FIG. 9 is a schematic illustration of a projected object generated by the processor of FIG. 1 following the projection operation of FIG. 8.

In some embodiments of the present technology, in order to generate the 3D-platform representation 1600 of the given tooth-specific platform, the processor 150 of the computer system 200 (e.g., the processor 150 of the interface device 210) may be configured to acquire a 3D-tooth representation 700, depicted in FIG. 7, of a given tooth on which the given tooth-specific platform is to be attached.

In some embodiments, the processor 150 may acquire the 3D-tooth representation 700 from the imaging device 220. For example, the imaging device 220 may capture the 3D image 300 (see FIG. 3) and may transmit the information indicative of the 3D image 300, which includes the 3D-tooth representation 700, to the processor 150 of the interface device 210. In other embodiments, the processor 150 may acquire the 3D-tooth representation 700 from an external/remote computer system. For example, the processor 150 may acquire the 3D-tooth representation 700 via the communication network 240 of the computer system 200 from a computer system of an orthodontic clinic.

It should be noted that the 3D-tooth representation 700 is a 3D-tooth representation of the specific tooth to which the given tooth-specific platform is to be attached. For example, 3D-tooth representation 700 is generated based on the specific tooth of the patient and has a surface 701 corresponding to the surface of the specific tooth of the patient.

It should also be noted that 3D-tooth representation 700 has (i) a crown portion 702 that corresponds to a crown portion of the specific tooth, and (ii) a root portion 704 that corresponds to a root portion of the specific tooth.

It is contemplated that in some embodiments of the present technology, the processor 150 may acquire only a portion of 3D-tooth representation 700 for the purpose of generating the 3D-platform representation 1600. For instance, the processor 150 may acquire only the crown portion 702 of the 3D-tooth representation 700, while not acquiring the root portion 704 of the 3D-tooth representation 700.

As such, it can be said that in at least some embodiments of the present technology, the processor 150 may be configured to acquire at least a portion of the 3D-tooth representation 700 for the purpose of generating the 3D-platform representation 1600.

The processor 150 is also configured to define an attachment zone 750 on the surface 701 of the 3D-tooth representation 700. As seen, the attachment zone 750 has a zone perimeter 760 and encloses a surface portion 770 of the surface 701 of the 3D-tooth representation 700. The surface portion 770 corresponds to a surface portion of the specific tooth to which the given tooth-specific platform is to be attached.

It is contemplated that the processor 150 may be configured to define the attachment zone 750 in different manners. However, in at least some embodiments of the present technology, in order to define the attachment zone 750, the processor 150 may be configured to (i) define an attachment point 780 of the surface 701 of the 3D-tooth representation 700, and (ii) use the attachment point 780 for defining the zone perimeter 760 of the attachment zone 750. For example, the processor 150 may use the attachment point 780 for defining the zone perimeter 760 of the attachment zone 750 such that the attachment point 780 is enclosed by the zone perimeter 760.

In at least some embodiments of the present technology, the processor 150 may use the attachment point 780 for defining the zone perimeter 760 by (i) determining a minimum area for attaching the given tooth-specific platform on the specific tooth, and (ii) defining the zone perimeter 760 around the attachment point 780 such that it encloses the surface portion 770 having at least that minimum area. Alternatively, a skilled professional may define the attachment point 780 and/or the zone perimeter 760 of the attachment zone 750 and/or may provide input to the computer system 200 for allowing the processor 150 to define the attachment point 780 and/or the zone perimeter 760 of the attachment zone 750, without departing from the scope of the present technology.

It should be noted that, for the purpose of generating the 3D-platform representation 1600 (see FIG. 16), the processor 150 may be configured to generate an intermediary 3D representation (e.g., intermediary 3D object). This means that, for the purpose of generating the 3D-platform representation 1600, the processor 150 may be configured to:
generate a projected object, such as a projected object 900 depicted in FIG. 9, for example;
use (i) the zone perimeter 760 and (ii) the projected object 900 for generating a surface, such as a tooth-oriented surface 1302 depicted in FIG. 11, for example;
use the tooth-oriented surface 1302 for generating an intermediary 3D object, such as a preliminary 3D-platform representation 1300 depicted in FIG. 13, for example; and
use (i) the intermediary 3D object, and (ii) the 3D-tooth representation 700 for generating the 3D-platform representation 1600 of the given tooth-specific platform.

How the processor 150 is configured to perform the immediately-above list of processing operations will now be discussed in turn.

Figure 11:
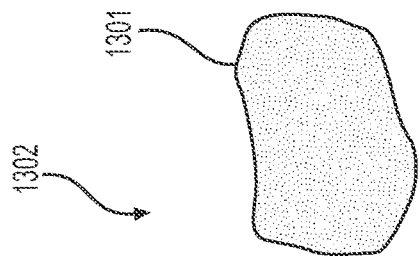
FIG. 11 is a schematic illustration of a tooth-oriented surface generated by the processor of FIG. 1 following the cutting operation of FIG. 10.

Reference to FIGS. 8 to 11 will now be made for describing generation of the tooth-oriented surface 1302 depicted in FIG. 11.

Figure 8:
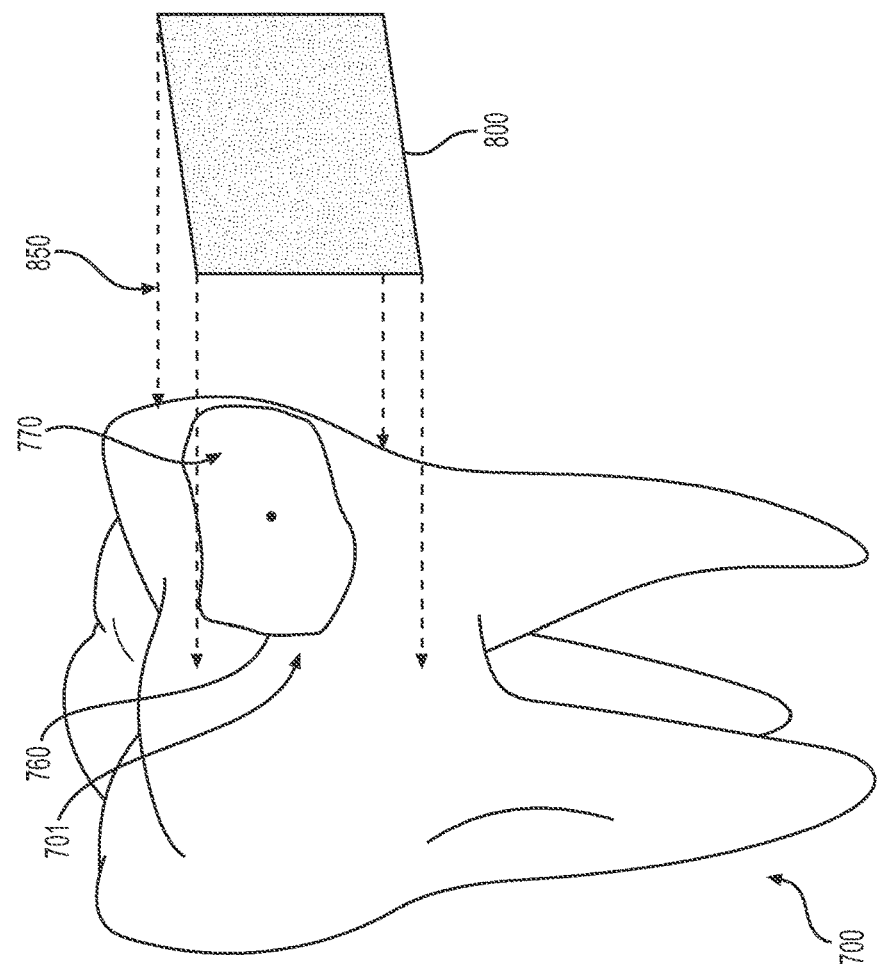
FIG. 8 is a schematic illustration of a projection operation performed by the processor of FIG. 1 onto a print object against the 3D-tooth representation of FIG. 7.

The processor 150 may be configured acquire a print object 800 depicted in FIG. 8. Broadly speaking, the print object 800 is an object representative of print elements that are to be used for a tooth-oriented surface of the given tooth-specific platform. For example, the print object 800 may be representative of a print element such as a tooth number of the specific tooth to which the given tooth-specific platform is to be attached. In some cases, it may be desirable to have the tooth number on the tooth-oriented surface of the given tooth-specific platform. In another example, the print object 800 may be representative of a grid-like relief. As it will become apparent from the description herein further below, the grid-like relief of the print object 800 may be useful for increasing the surface area of a tooth-oriented surface of the given tooth-specific platform, which may in turn allow introduction of a larger amount of adhesive material between the tooth-oriented surface and the surface of the specific tooth.

The processor 150 may be configured to perform a projection operation 850 on the print object 800 and against the surface 701. Put another way, the processor 150 may be configured to project the print object 800 onto the surface 701, thereby generating the projected object 900, depicted in FIG. 9, which conforms to the surface of 701.

It is contemplated that the processor 150 may perform the projection operation 850 on the print object 800, such that the projected object 900 is superimposed over a totality of the surface portion 770. Put another way, when the projected object 900 is so-generated by the processor 150, the projected object 900 conforming to the surface 701 completely covers the surface portion 770 enclosed by the zone perimeter 760.

It should be noted that once the processor 150 so-generates the projected object 900, the print elements and the grid-type relief of the print object 800 are projected onto the surface 701 and, thereby become projected print elements and projected grid-type relief on the projected object 900.

It is contemplated that the print object 800 may be a 3D object. However, it is also contemplated that the print object 800 may be a 2D object, such as a surface for example, represented in 3D space. In some embodiments, it is contemplated that the print object 800 may be an object without print elements and/or grid-type relief. As such, it is contemplated that the projected object 900 may or may not have projected print elements and/or projected grid-type relief, without departing from the scope of the present technology.

Figure 10:
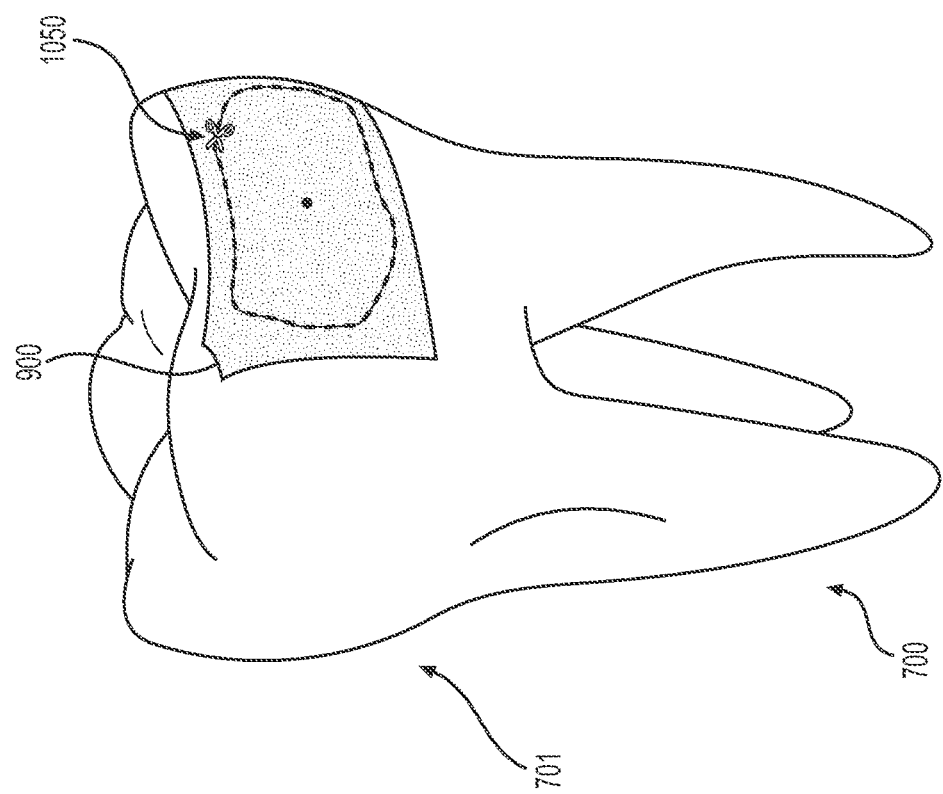
FIG. 10 is a schematic illustration of a cutting operation performed by the processor of FIG. 1 on the projected object of FIG. 9.

With reference to FIG. 10, the processor 150 may then be configured to perform a "cutting" operation 1050 (illustrated as a pair of scissors in FIG. 10) on the projected object 900. Put another way, the processor 150 may be configured to "cut" the projected object 900 using the zone perimeter 760 as a cutting trajectory. It is contemplated that the cutting operation 1050 may be performed by the processor 150 as one or more boolean operations between the projected object 900 and the zone perimeter 760.

It should be noted that by performing the cutting operation 1050, the processor 150 generates/defines the tooth-oriented surface 1302 depicted in FIG. 11. The tooth-oriented surface 1302 has a perimeter 1301 that matches/conforms to the zone perimeter 760. Put another way, the tooth-oriented surface 1302 can be said to be a portion of the projected object 900 that is enclosed within the zone perimeter 760.

In summary, it contemplated that in order to generate the tooth-oriented surface 1302 the processor 150 may be configured to: (i) acquire the print object 800 in FIG. 8, (ii) perform the projection operation 850 onto the print object 800, thereby generating the projected object 900 matching/conforming to the surface 701 on which the print object 800 is projected, and (iii) perform the cutting operation 1050 (e.g., one or more boolean operation between the projected object 900 and the zone perimeter 760) in FIG. 10, thereby generating the tooth-oriented surface 1302.

Figure 13:
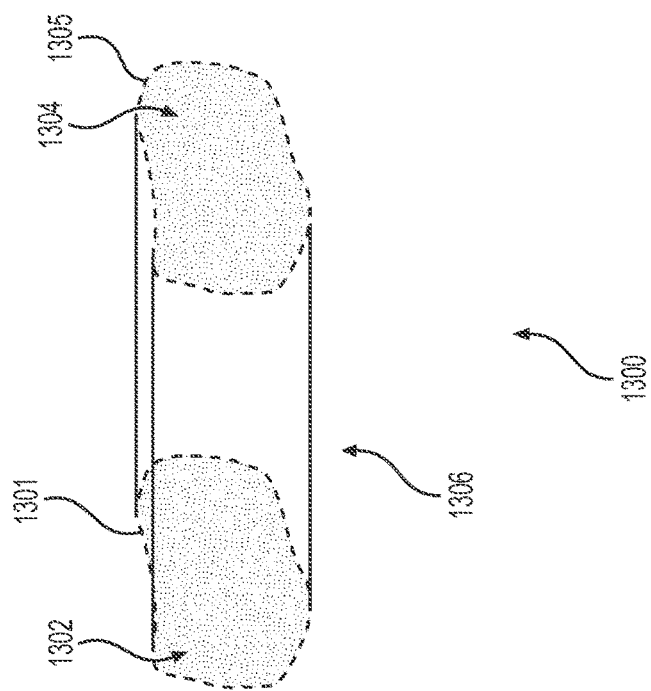
FIG. 13 is a schematic illustration of a preliminary 3D-platform representation generated by the processor of FIG. 1.
Figure 12:
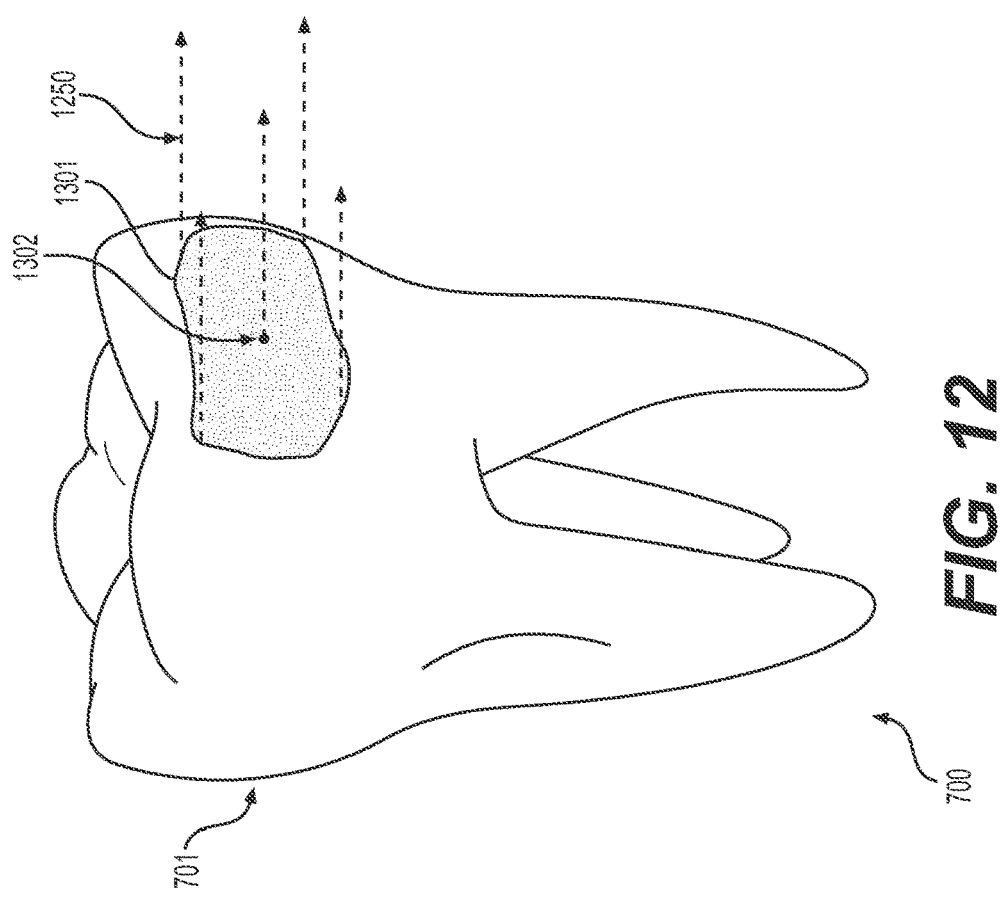
FIG. 12 is a schematic illustration of an extrusion operation performed by the processor of FIG. 1 on the tooth-oriented surface of FIG. 11.

As mentioned above, the processor 150 may be configured to use the tooth-oriented surface 1302 for generating the intermediary 3D object (e.g., a preliminary 3D-platform representation 1300 depicted in FIG. 13). Reference to FIGS. 12 and 13 will now be made for describing generation of the intermediary 3D object such as the preliminary 3D-platform representation 1300.

As shown in FIG. 12, the processor 150 may be configured to perform an extrusion operation 1250 on the tooth-oriented surface 1302. The extrusion of the tooth-oriented surface 1302 may be performed in a pre-determined direction. For example, the direction of the extrusion operation 1250 may be determined as a normal direction to one or more surface elements of the tooth-oriented surface 1302.

It should be noted that by performing the extrusion operation 1250, the processor 150 generates/defines the intermediary 3D object (e.g., the preliminary 3D-platform representation 1300) depicted in FIG. 13. The so-generated preliminary 3D-platform representation 1300 has the tooth-oriented surface 1302, an other surface 1304, and a preliminary perimeter wall 1306. The tooth-oriented surface 1302 has a perimeter 1301 and the other surface 1204 has a perimeter 1305. A cross-sectional profile of the so-generated preliminary 3D-platform representation 1300 matches/conforms to the profile of the attachment zone 750. Put another way, both the perimeter 1301 and the perimeter 1305 match/conform to the zone perimeter 760. The preliminary perimeter wall 1306 extends (i) between the tooth-oriented surface 1302 and the other surface 1304 (ii) in the direction that is used for preforming the extrusion operation 1250.

Recalling that the tooth-oriented surface 1302 is a portion of the projected object 900, it should be noted that in some embodiments of the present technology, the tooth-oriented surface 1302 may have at least a portion of the projected print elements and/or at least a portion of the projected grid-type relief of the projected object 900. The at least the portion of the projected print elements and/or the at least the portion of the projected grid-type relief of the projected object 900 that may be on the tooth-oriented surface 1302 are portions of the projected print elements and/or of the projected grid-type relief that are located on a section of the projected object 900 that covers the attachment zone 750.

In summary, the processor 150 may be configured to perform the extrusion operation 1250 on the tooth-oriented surface 1302, thereby generating the preliminary 3D-platform representation 1300 depicted in FIG. 13.

Figure 15:
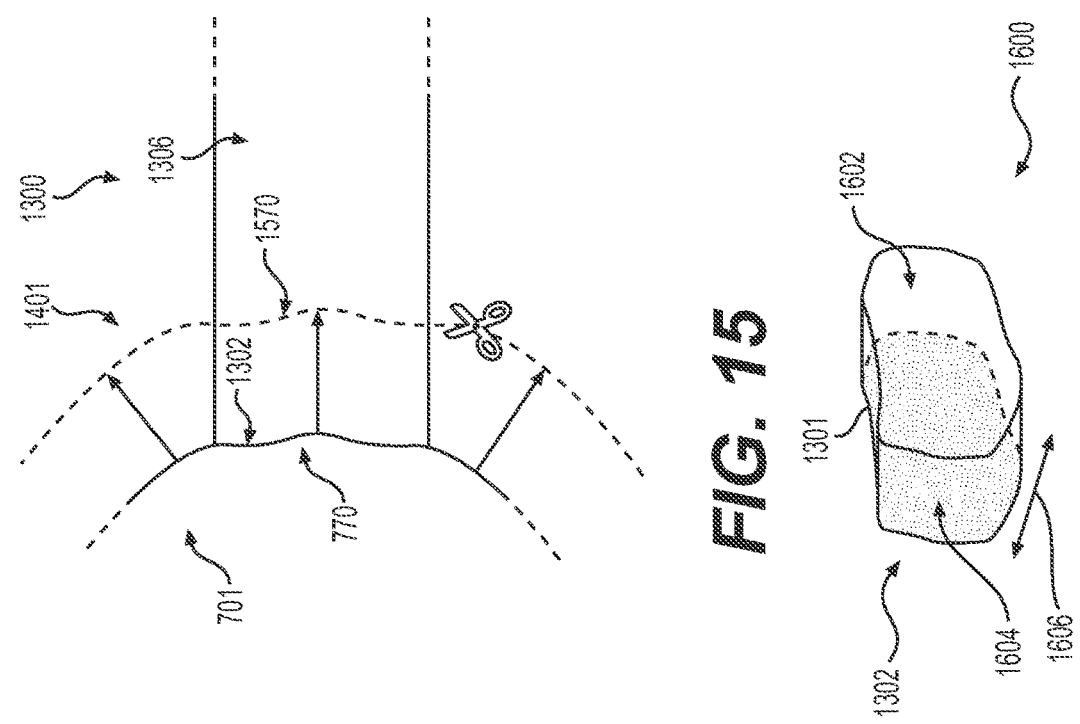
FIG. 15 is a cross-sectional view of the 3D-tooth representation of FIG. 7, an expanded 3D-tooth representation and of the preliminary 3D-platform representation of FIG. 13, taken though line 15-15 of FIG. 14.
Figure 16:
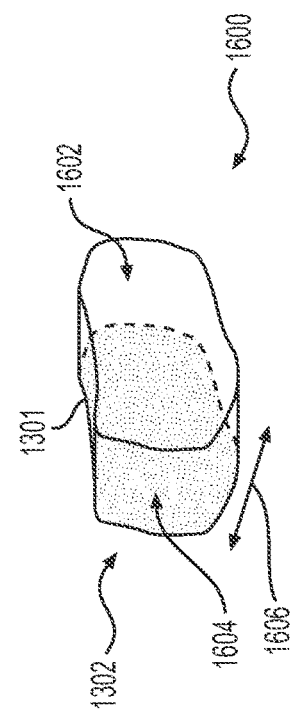
FIG. 16 is a schematic illustration of a 3D-platform representation generated by the processor of FIG. 1 in accordance with at least some embodiments of the present technology.
Figure 14:
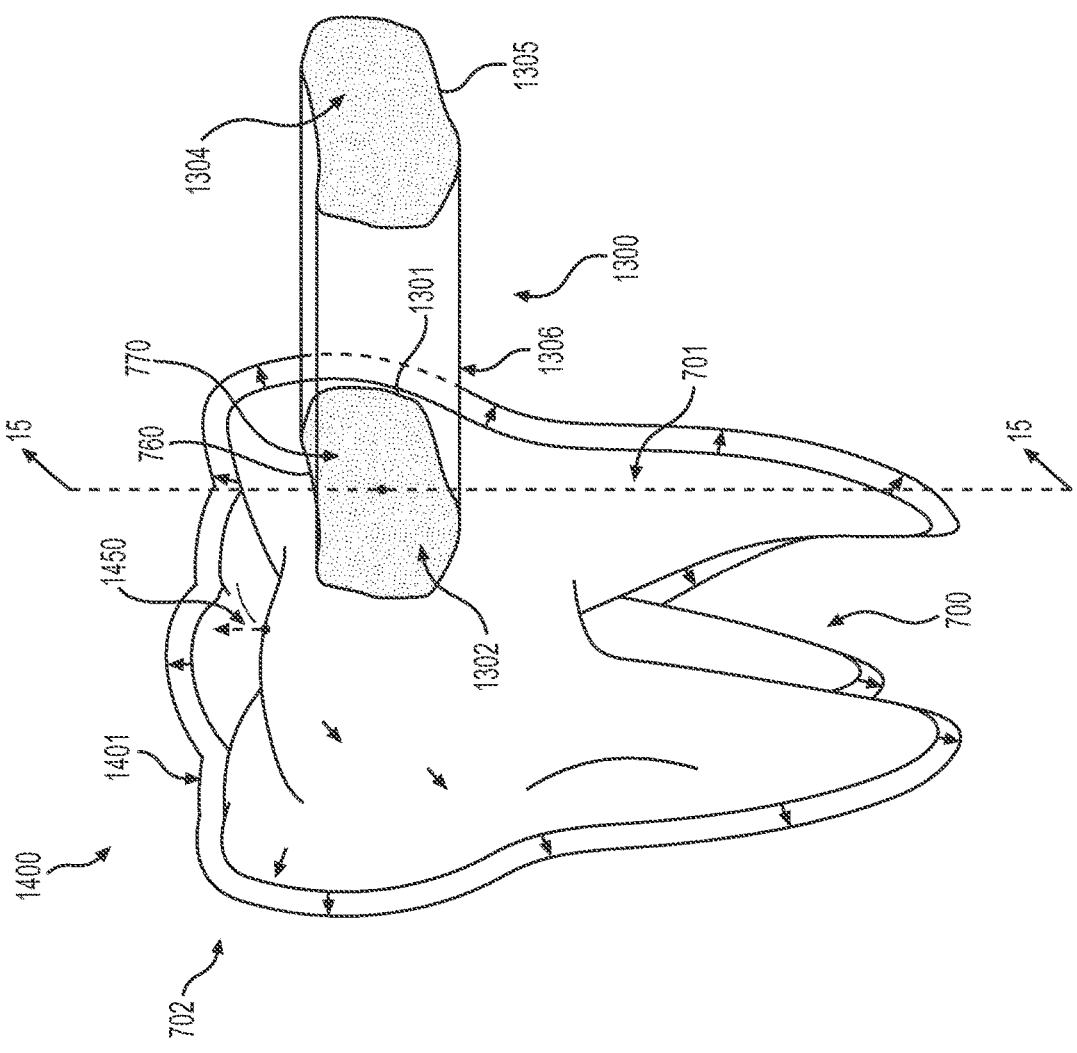
FIG. 14 is a schematic illustration of an expansion operation performed by the processor of FIG. 1 on the 3D-tooth representation of FIG. 7.
Figure 17:
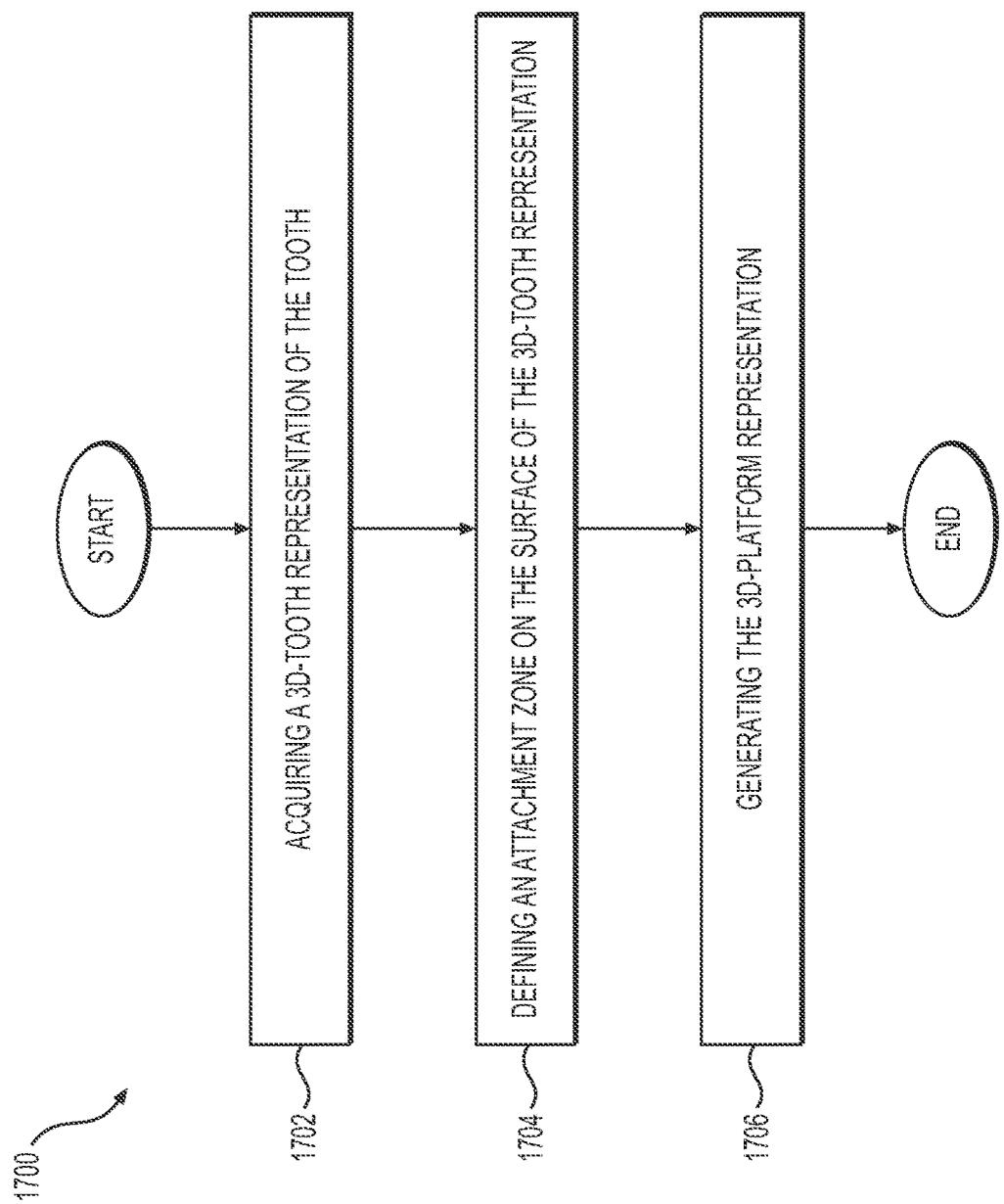
FIG. 17 is a schematic illustration of a method of generating the 3D-platform representation executable by the processor of FIG. 1 in accordance with at least some embodiments of the present technology.

As mentioned above, the processor 150 may be configured to use the intermediary 3D object (e.g., the preliminary 3D-platform representation 1300) and the 3D-tooth representation 700 for generating the 3D-platform representation 1600 of the given tooth-specific platform. Reference to FIGS. 14 to 16 will now be made for describing generation of the 3D-platform representation 1600 based on the preliminary 3D-platform representation 1300 and the 3D-tooth representation 700.

With reference to FIG. 14, the processor 150 may be configured to perform an expansion operation 1450 on the 3D-tooth representation 700 (and/or on at least a portion thereof, such as solely on the crown portion 702 and/or solely on the surface portion 770 of the surface 701). In other words, the processor 150 may be configured to expand the 3D-tooth representation 700 having the surface 701 by a pre-determined distance, and thereby generate an expanded 3D-tooth representation 1400 having an expanded surface 1401. For example, the surface 701 may be expanded by the pre-determine distance outwardly from the 3D-tooth representation 700 along normal directions of surface elements of the surface 701.

In some embodiments of the present technology, the pre-determined distance of expansion of the surface 701 may be equal to a thickness 1606 of the 3D-platform representation 1600 (e.g., desired thickness of the tooth-specific platform) as it will become apparent from the description herein below.

With reference to FIG. 15, there is depicted a cross-sectional view of (i) the surface 701, (ii) the expanded surface 1401, and (iii) the preliminary 3D-platform representation 1300, taken through a line 15-15 depicted in FIG. 14. As it can be seen, the expanded surface 1401 of the expanded 3D-tooth representation 1400 does not match/conform to the surface 701 of the 3D-tooth representation 700 due to the expansion operation 1450.

The purpose of so-generating the expanded surface 1401 is to use the expanded surface 1401 by the processor 150 as a cutting trajectory for "cutting" the preliminary 3D-platform representation 1300 along the preliminary perimeter wall 1306. This other cutting operation (illustrated as another pair of scissors in FIG. 15) by the processor 150 may be performed as one or more boolean operation between the intermediary 3D object (e.g., the preliminary 3D-platform representation 1300) and the expanded surface 1401, such that the one ore more boolean operation result in generation of the 3D-platform representation 1600 depicted in FIG. 16.

The 3D-platform representation 1600 has the tooth-oriented surface 1302, a tooth-opposite surface 1602, and a perimeter wall 1604. It should be noted that the tooth-opposite surface 1602 does not match/conform to the tooth-oriented surface 1302. Indeed, as mentioned above, the tooth-oriented surface 1302 matches/conforms to the surface portion 770 of the surface 701 of the 3D-tooth representation 700, while the tooth-opposite surface 1602 matches an expanded surface portion 1570. The expanded surface portion 1570 can be said to be a given expanded surface portion of the 3D-tooth representation 700 and/or a given surface portion of the expanded 3D-tooth representation 1400.

It is contemplated that the computer system 200 may be configured to generate a 3D-platform representation corresponding to the tooth-specific platform 680 depicted in FIG. 6 similarly to how the computer system 200 is configured to generate 3D-platform representation 1600 depicted in FIG. 16 of the given tooth-specific platform.

Design Process of the Tooth-Specific Bracket

A process of designing of a given tooth-specific bracket will now be discussed with reference to FIGS. 18 to 30. More particularly, how the computer system 200 is configured to generate a 3D-bracket representation 3000 depicted in FIG. 30 corresponding to the given tooth-specific bracket will now be discussed.

Figure 30:
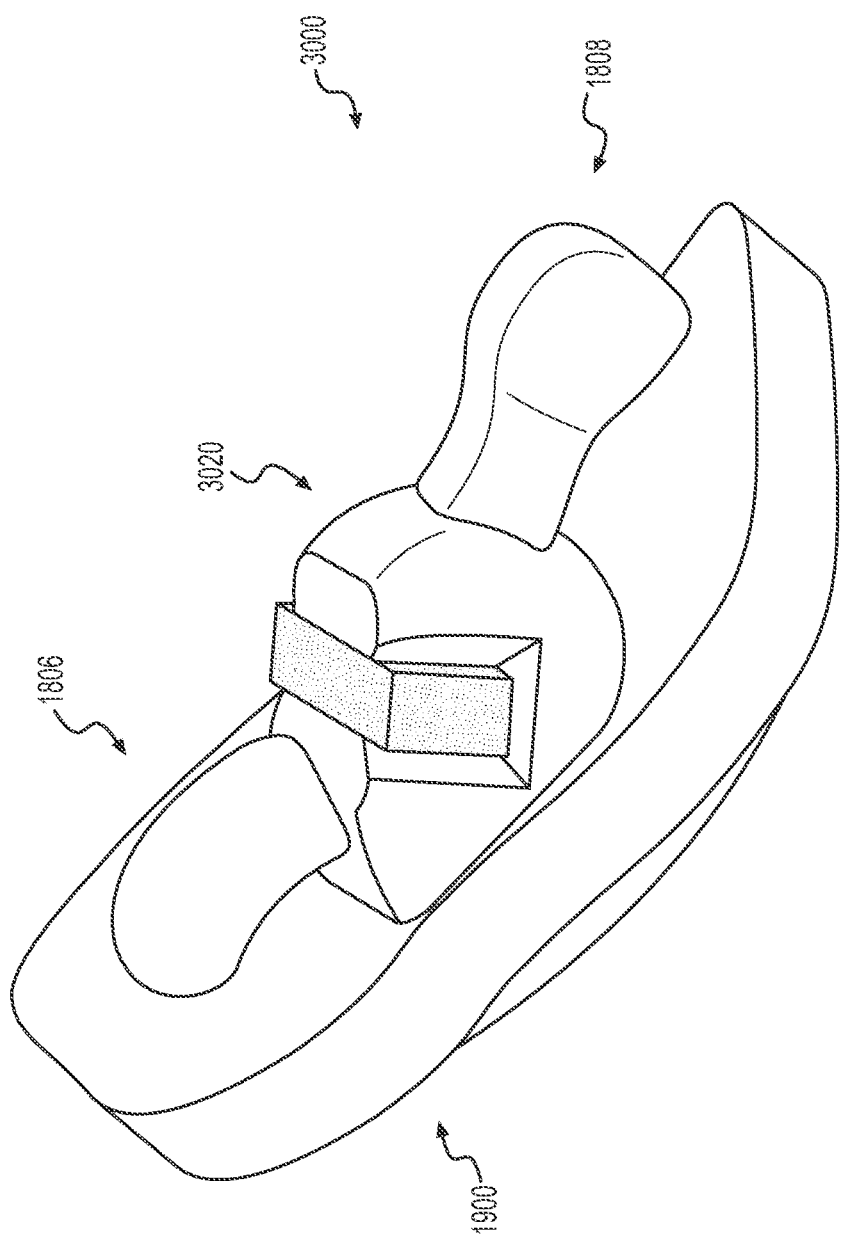
FIG. 30 is a schematic illustration of the 3D-bracket representation of the given tooth-specific bracket, in accordance with at least some embodiments of the present technology.

Broadly speaking, the 3D-bracket representation 3000 in FIG. 30 is depicted with a 3D-platform representation 1900 corresponding to a respective tooth-specific platform to which the given tooth-specific bracket is to be attached. The 3D-bracket representation 3000 comprises a set of components: a 3D-grooved body representation 3020 corresponding to the grooved body of the given tooth-specific bracket, as well as a first 3D-arm representation 1806 and a second 3D-arm representation 1808 corresponding to the pair of holding arms of the given tooth-specific bracket.

As it will become apparent from the description herein further below, at least some components of the 3D-bracket representation 3000 may be individually positioned by the processor 150 relative to the 3D-platform representation 1900 and/or relative to other components of the 3D-bracket representation 3000. Put another way, the at least some components of the 3D-bracket representation 3000 may be positioned one-by-one by the processor 150 relative to the 3D-platform representation 1900 and/or relative to other components of the 3D-bracket representation 3000. It can also be said that, instead of acquiring a pre-assembled 3D-bracket representation and then positioning this pre-assembled 3D-bracket representation as a whole relative to the 3D-platform representation 1900, the processor 150 may be configured to:

(i) acquire various components of the 3D-bracket representation 3000 individually (one-by-one) from a storage;
(ii) position the acquired components individually (one-by-one) relative to the 3D-platform representation 1900 and/or relative to other components of the 3D-bracket representation 3000; and
(iii) adjust the above-mentioned positions individually (one-by-one) relative to the 3D-platform representation 1900 and/or relative to other components of the 3D-bracket representation 3000, such that their adjusted positions correspond to positions of the corresponding components of the given tooth-specific bracket relative to the respective tooth-specific platform when attached to the respective tooth-specific platform.

Figure 18:
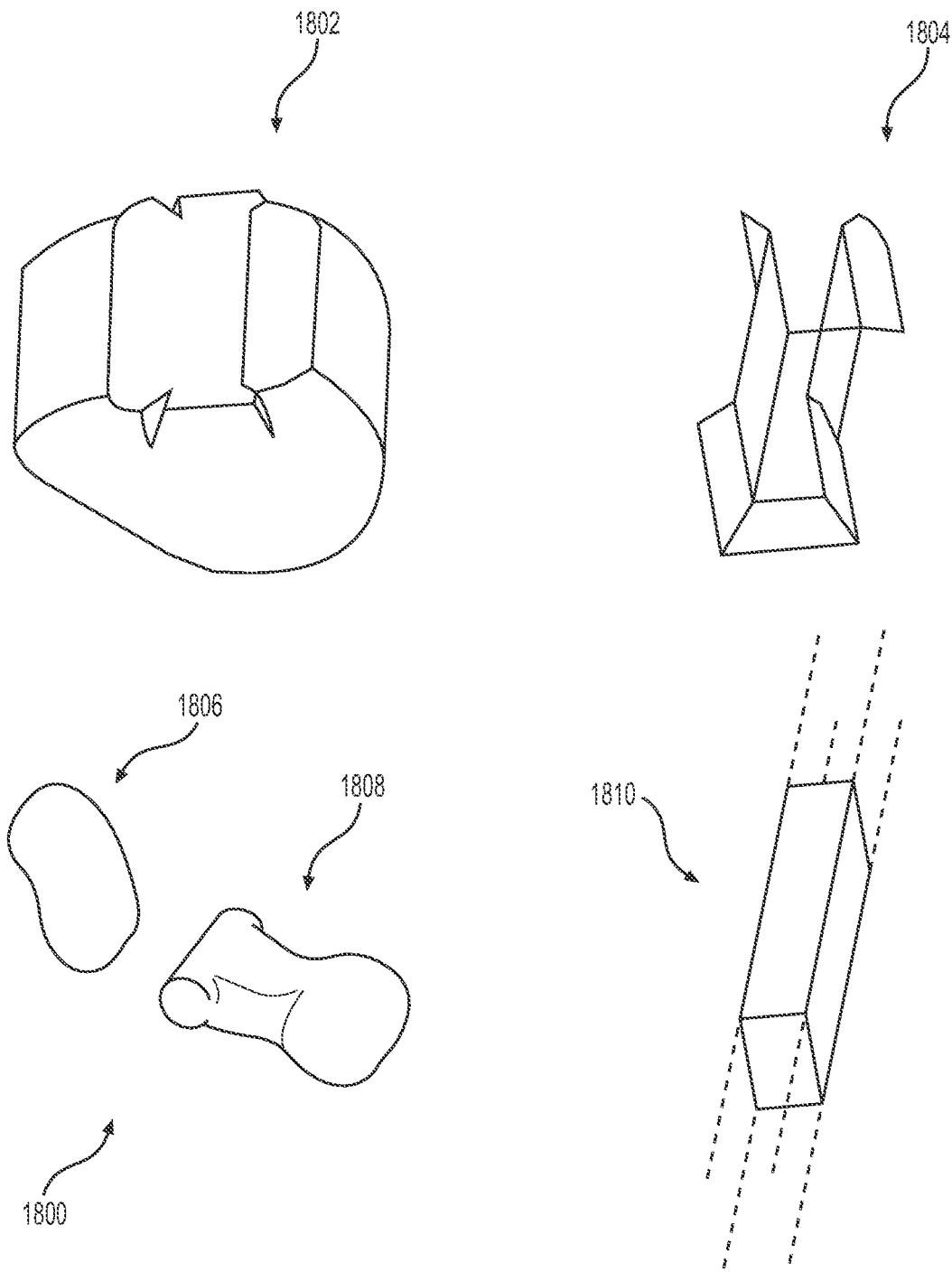
FIG. 18 is a schematic illustration of 3D representations of at least some components of a dental appliance, such as a tooth-specific bracket, and of an archwire, in accordance with at least some embodiments of the present technology.

With reference to FIG. 18, there are depicted 3D representations that the processor 150 may be configured to acquire for generating the 3D-bracket representation 3000. As it can be seen, the processor 150 may be configured to acquire (i) a 3D-body structure representation 1802, (ii) a 3D-groove structure representation 1804, (iii) the first 3D-arm representation 1806, (iv) the second 3D-arm representation 1808, and (v) a 3D-archwire representation 1810. It should be noted that, although the 3D-archwire representation 1810 does not per se correspond to a components of the given tooth-specific brackets, the processor 150 may still be configured to acquire it in at least some embodiments of the present technology.

It is contemplated that in at least some embodiments of the present technology, the processor 150 may be configured to acquire the 3D representations for generating the 3D-bracket representation 3000 from a library. Broadly speaking, the library may be embodied on any storage medium that is communicatively coupled with the processor 150 and that includes pre-stored 3D representations of components of various dental appliances. It is contemplated that the library may be a local library, for example embodied on a given storage medium of the computer system 200. It is also contemplated that library may be a remote/external library, for example embodied on a given storage medium of an remote/external computer system.

The processor 150 may acquire the 3D representations depicted in FIG. 18 individually. This means that the processor 150 may acquire the 3D representations of FIG. 18 independently from one another. In one case, the 3D representations depicted in FIG. 18 may be pre-stored separately in the library, in a form of distinct digital files, for example, that the processor 150 may acquire separately from one another.

It is contemplated that the processor 150 may acquire the 3D-body structure representation 1802 and the 3D-groove structure representation 1804 for generating the 3D-grooved body representation 3020 of the 3D-bracket representation 3000. For example, the 3D-body structure representation 1802 may correspond to a pre-determined shape of the grooved body of the given tooth-specific bracket, while the 3D-groove structure representation 1804 may correspond to a pre-determined groove shape in the grooved body of the given tooth-specific bracket. As such, in some embodiments, the processor 150 may be configured to perform one or more boolean operations between the 3D-body structure representation 1802 and the 3D-groove structure representation 1804, thereby generating the 3D-grooved body representation 3020. However, it is contemplated that in some embodiments the processor 150 may acquire the 3D-grooved body representation 3020 directly from the library as a single 3D representation.

Figure 19:
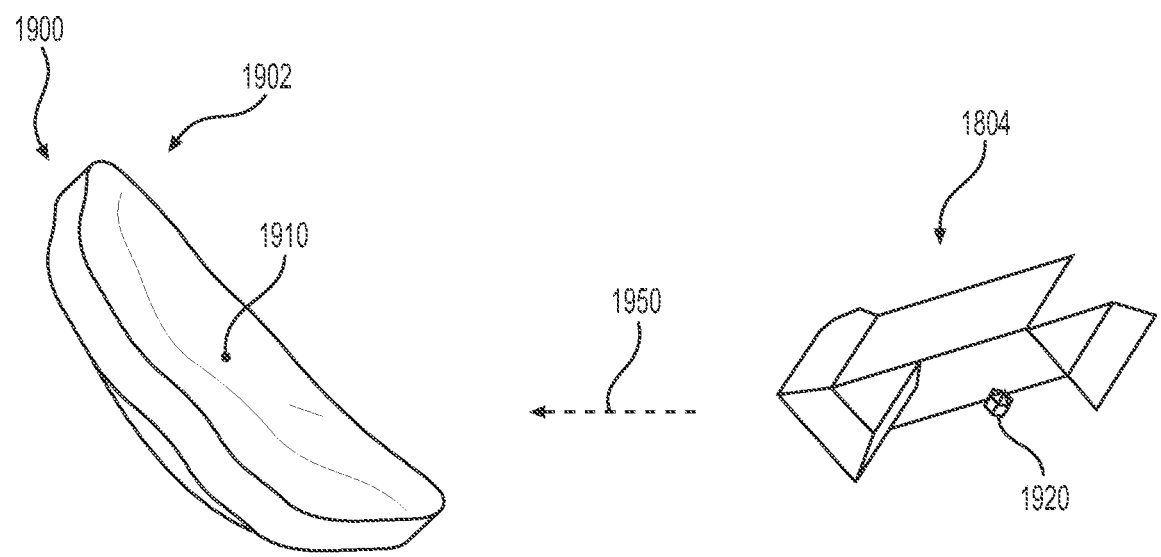
FIG. 19 is a schematic illustration of a positioning operation between a 3D-groove body representation and a 3D-platform representation, in accordance with at least some embodiments of the present technology.

With reference to FIG. 19, the processor 150 may also acquire the 3D-platform representation 1900 from the library. However, in other embodiments of the present technology, the 3D-platform representation 1900 may be generated by the processor 150 similarly to how the 3D-platform representation 1600 is generated by the processor 150, without departing from the scope of the present technology.

As it will be described herein further below, the processor 150 is not only configured to generate the 3D-bracket representation 3000, but may also be configured to position (and adjust positions of) some components of the 3D-bracket representation 3000 relative to the 3D-platform representation 1900 and/or to other components of the 3D-bracket representation 3000 such that their adjusted positions correspond to positions of corresponding components of the given tooth-specific bracket when attached to the 3D-platform representation 1900.

To that end, the processor 150 may be configured to perform a positioning operation 1950 between the 3D-platform representation 1900 and the 3D-groove structure representation 1804. For example, as seen in FIG. 19, the 3D-platform representation has a tooth-opposite surface 1902 corresponding to a tooth-opposite surface of the respective tooth-specific platform to which the given tooth-specific bracket is to be attached.

In order to perform the positioning operation 1950, the processor 150 may be configured to define a first attachment point 1910 on the tooth-opposite surface 1902 of the 3D-platform representation 1900 and a second attachment point 1920 on the 3D-groove structure representation 1804. For example, a position of the first attachment point 1910 on the tooth-opposite surface 1902 and a position of the second attachment point 1920 on the 3D-groove structure representation 1804 may be inputted by a skilled professional so that the processor 150 may define them respectively on 3D-platform representation 1900 and on the 3D-groove structure representation 1804.

Figure 20:
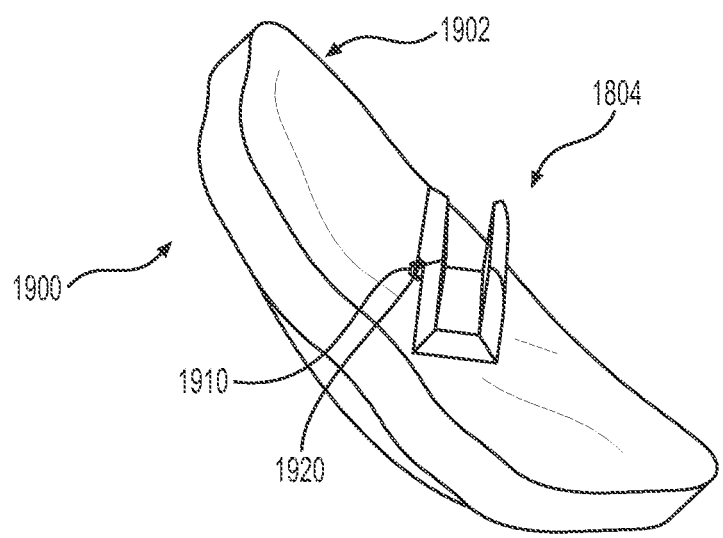
FIG. 20 is a schematic illustration of an outcome of the positioning operation of FIG. 19.

It can be said that the processor 150 performing the positioning operation 1950 is configured to position the 3D-groove structure representation 1804 relative to the 3D-platform representation 1900 such that the first attachment point 1910 and the second attachment point 1920 coincide with one another, such as depicted in FIG. 20.

It is contemplated that in some embodiments, once the first attachment point 1910 and the second attachment point 1920 coincide with one another, the 3D-groove structure representation 1804 may be further oriented by the processor 150. For example, the 3D-groove structure representation 1804 may be oriented such that the corresponding void is oriented so as to conform to a trajectory of the respective archwire that is to be received in the corresponding void.

Figure 21:
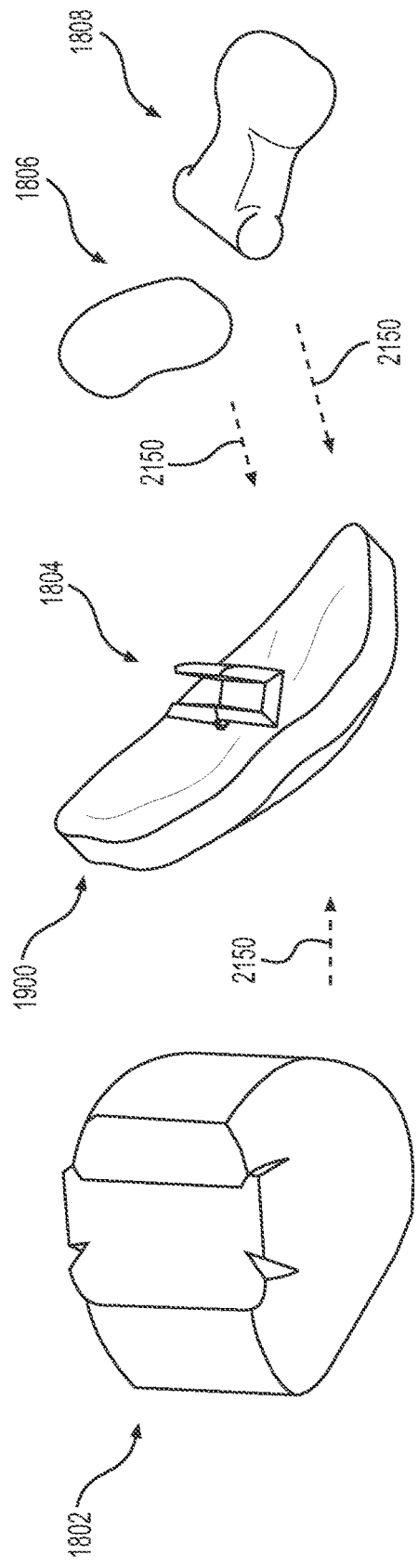
FIG. 21 is a schematic illustration of initial positioning operation between at least some components of a 3D-bracket representation of FIG. 30 and the 3D-platform representation of FIG. 19, in accordance with at least some embodiments of the present technology.
Figure 22:
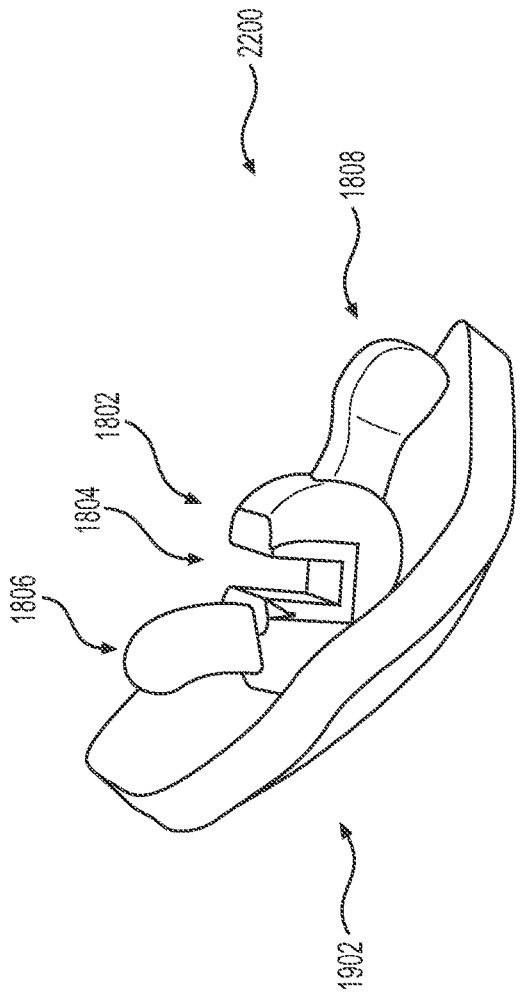
FIG. 22 is a schematic illustration of an initial configuration of the 3D-bracket representation of FIG. 30 after the initial positioning operation of FIG. 21.

With reference to FIG. 21, the processor 150 may be configured to perform an initial positioning operation 2150 between the 3D-platform representation 1900 and the positioned 3D-groove structure representation 1804 and (i) the 3D-body structure representation 1802, (ii) the first 3D-arm representation 1806 and (iii) the second 3D-arm representation 1808. For example, by performing the initial positioning operation 2150, the processor 150 may be configured to generate an initial configuration 2200 depicted in FIG. 22 of the components of the 3D-bracket representation 3000 and of the 3D-platform representation 1900.

As mentioned above, instead of acquiring the 3D-groove structure representation 1804 and the 3D-body structure representation 1802 separately, the processor 150 may acquire the 3D-grooved body representation 3020. Hence, in some embodiments, instead of defining the second attachment point 1920 on the 3D-groove structure representation 1804 as depicted in FIGS. 19 to 21, the processor 150 may be configured to define a second attachment point (not depicted) on the 3D-grooved body representation 3020 and perform a positioning operation between the 3D-platform representation 1900 and the 3D-grooved body representation 3020 such that the first attachment point 1910 and the second attachment point of the 3D-grooved body representation 3020 coincide with one another.

In embodiments where the processor 150 is configured to acquire the 3D-grooved body representation 3020 (instead of acquiring the 3D-groove structure representation 1804 and the 3D-body structure representation 1802 separately), the processor 150 may be configured to perform the initial positioning operation 2150 only on the first 3D-arm representation 1806 and the second 3D-arm representation 1808.

With reference to FIG. 23 to FIG. 29, there is depicted a set of ghost arms 2306 and 2308, and more specifically, a first ghost arm 2306 associated with the first 3D-arm representation 1806 and a second ghost arm 2308 associated with the second 3D-arm representation 1808. Each of the set of ghost arms 2306 and 2308 is offset from the associated one of the first 3D-arm representation 1806 and the second 3D-arm representation 1808 by a distance that is representative of a thickness of a ligature to be used. In other words, the distance between the set of ghost arms 2306 and 2308 and the first 3D-arm representation 1806 and the second 3D-arm representation 1808 is sufficient for accepting the ligature (in use) between set of ghost arms 2306 and 2308 and a surface of a 3D-platform representation 1900.

Broadly speaking, the purpose of the ghost arms 2306, 2308 is to ensure that a space for the installation of ligatures that are used to hold the arc is provided for, as the first 3D-arm representation 1806 and the second 3D-arm representation 1808 are being positioned relative to the 3D-body structure representation 1802. By using the ghost arms 2306, 2308, the processor 150 can ensure that the space between the surface of the 3D-platform representation 1900 (a plane that is depicted schematically at 2406 in FIG. 24) and the first 3D-arm representation 1806 and the second 3D-arm representation 1808 is sufficient.

Figure 24:
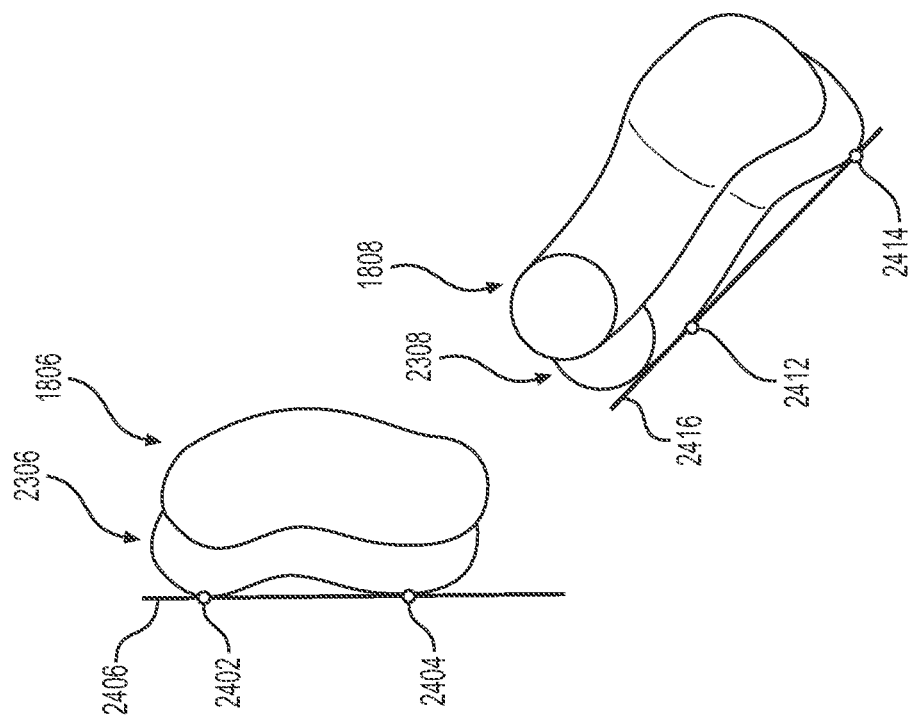
FIG. 24 is a schematic illustration of the ensemble of the first 3D-arm representation 1806 and the second 3D-arm representation with associated ghost arms positioned relative to a surface of a 3D-platform representation.
Figure 23:
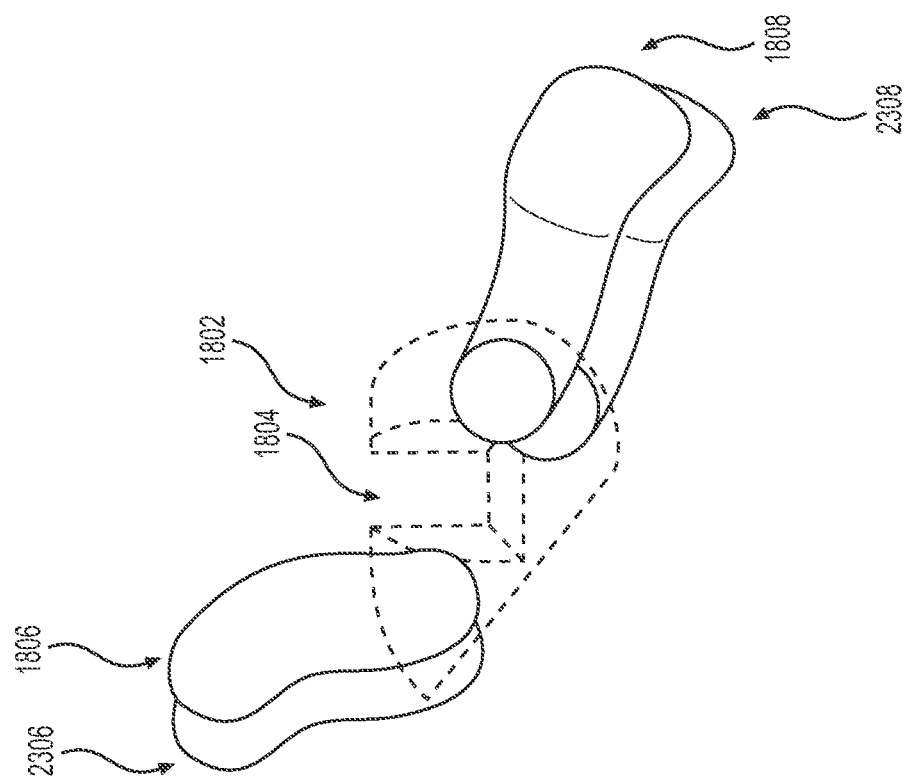
FIG. 23 is a schematic illustration of an ensemble of a first 3D-arm representation 1806 and a second 3D-arm representation with associated ghost arms implemented in accordance with at least embodiments of the present technology.

As is seen in FIG. 24, there are provided anchor points 2402, 2404, 2412, and 2414 on the ghost arms 2306 and 2308. The anchor points 2402, 2404, 2412, and 2414 are defined on the most outwardly concave portions of the ghost arms 2306, 2308 (two anchor points per each of the ghost arms 2306, 2308).

The purpose of the anchor points 2402, 2404, 2412, and 2414 is to check for contact occurring with the plane 2406, which plane 2406 is representative of the 3D-platform representation 1900.

The processor 150 first moves an ensemble of the first 3D-arm representation 1806 and the second 3D-arm representation 1808 and the associated ghost arms 2306, 2308 towards the 3D-platform representation 1900. Once the ensemble is sufficiently close to the 3D-platform representation 1900, the processor 150 checks for exact positioning of the ghost arms 2306, 2308 relative to the surface of the 3D-platform representation 1900. More specifically, using the anchor points 2402, 2404, 2412, and 2414, the processor 150 can position the ghost arms 2306, 2308 such that the anchor points 2402, 2404, 2412, and 2414 touch the surface of the 3D-platform representation 1900. In some embodiments of the present technology, the re-positioning is executed individually for the two 3D-arms and the associated ghost arms.

By doing so, the processor 150 can ensure that the actual arms (i.e. the first 3D-arm representation 1806 and the second 3D-arm representation 1808) are spaced away from the surface of the 3D-platform representation 1900 by the required distance to accommodate the ligature.

More specifically, in some embodiments of the present technology, the processor 150 may need to move the ghost arm closer to the surface of the 3D-platform representation 1900 (in those cases where the ensemble is away from the surface of the 3D-platform representation 1900) and in some cases the processor 150 may need to move the ghost arm away from the surface of the 3D-platform representation 1900 (in case there is a penetration therebetween).

Figure 25:
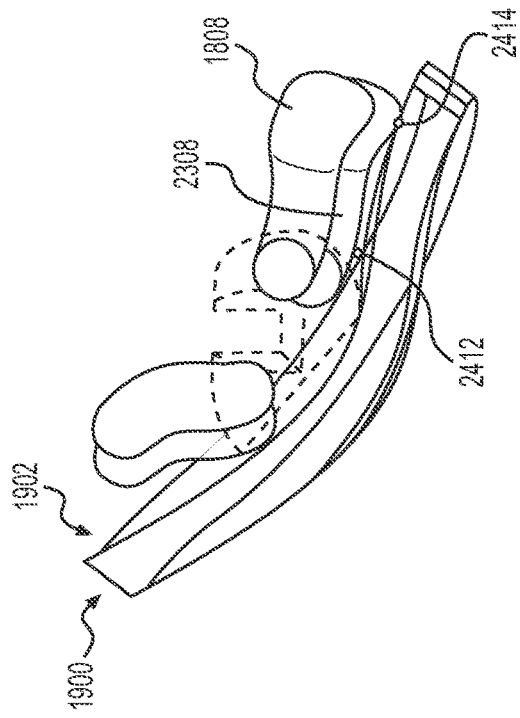
FIG. 25 to FIG. 28 depicts various stages of positioning and repositioning of the ensemble of the first 3D-arm representation and the second 3D-arm representation with associated ghost arms positioned relative to the surface of a 3D-platform representation.

FIG. 25 illustrates a result of the individually positioning, by the processor 150, the first 3D-arm representation 1806 and the second 3D-arm representation 1808 (together with the associated ghost arms 2306, 2308) relative to the 3D-platform representation using the respective pairs of platform anchor points 2402, 2404, 2412, and 2414 thereby defining (i) a preliminary position of the first 3D-arm representation 1806 and (ii) a preliminary position of the second 3D-arm representation 1808.

FIGS. 25 to 28 further depict various stages of the process of individually adjusting, by the processor 150, the respective preliminary position of the first 3D-arm representation 1806 and of the second 3D-arm representation 1808 relative to the 3D-grooved body representation using the respective adjustment anchor points 2402, 2404, 2412, and 2414.

Figure 26:
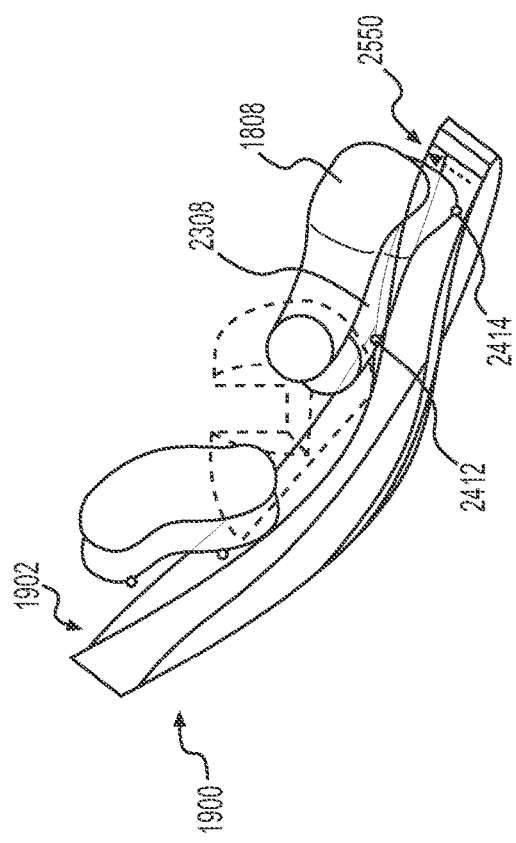

More specifically, FIG. 25 depicts a first adjustment 2550 away from the surface of the of the 3D-platform representation 1900 due to the penetration between the second 3D-arm representation 1808 and the 3D-platform representation 1900. FIG. 26 depicts a result of such the first adjustment 2550.

Figure 27:
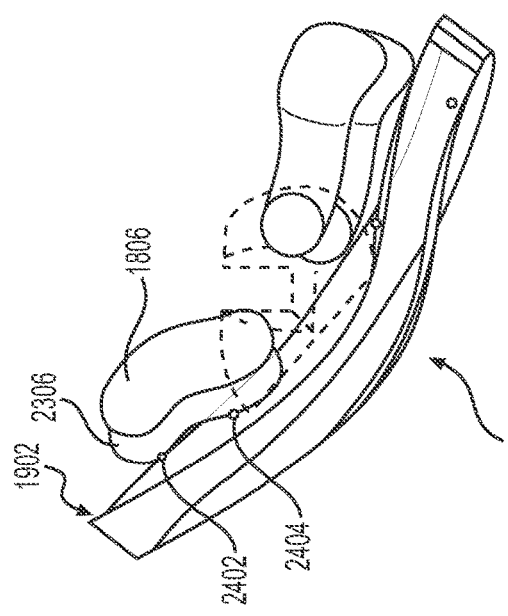
Figure 28:
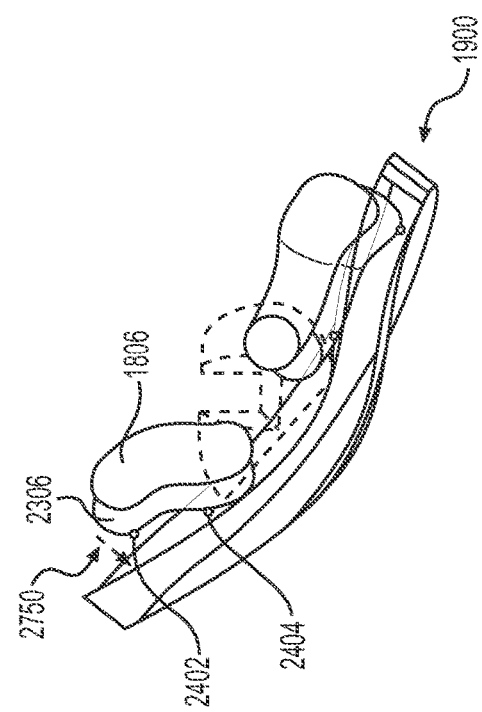

FIG. 27 depicts a second adjustment 2750 of the first 3D-arm representation 1806 towards the 3D-platform representation 1900 and FIG. 28 depicts a result 1906 of such the second adjustment 2750.

Even though not depicted, further adjustments may be required, for example, to the first 3D-arm representation 1806 away from the 3D-platform representation 1900.

Figure 29:
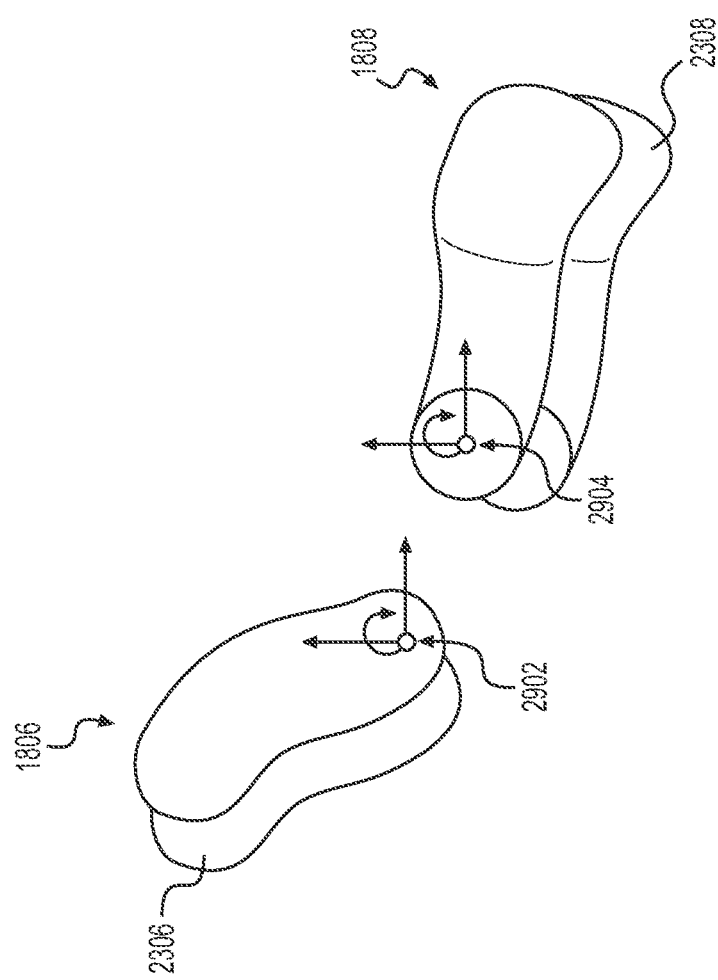
FIG. 29 is a schematic illustration a first direction of adjustment of the first 3D-arm representation towards the 3D-platform representation and a second direction of adjustment of the second 3D-arm representation.

FIG. 29 depicts schematically a first direction of adjustment 2902 of the first 3D-arm representation 1806 towards the 3D-platform representation 1900 and a second direction of adjustment 2904 of the second 3D-arm representation 1808.

How the computer system 200 is configured to manufacture the given tooth-specific platform and the given tooth-specific bracket will now be discussed.

Manufacturing the Tooth-Specific Platform and of the Tooth-Specific Bracket

As mentioned above, it is contemplated that the computer system 200 may be configured to manufacture tooth-specific platforms. This manufacture by the computer system 200 may be performed in a variety of ways.

In at least some embodiments of the present technology, the processor 150 of the computer system 200 may be configured to trigger manufacture of the given tooth-specific platform based on the 3D-platform representation 1600 depicted in FIG. 16. For example, the processor 150 may transmit to the manufacturing apparatus 230 (see FIG. 2) data representative of the 3D-platform representation 1600 and computer-readable instructions for triggering the manufacture of the given tooth-specific platform based on the 3D-platform representation 1600. In addition, it is also contemplated that the processor 150 may further transmit other data to the manufacturing apparatus, such as, for example, data indicative of type(s) of material(s) to be used for fabricating the given tooth-specific platform based on the 3D-platform representation 1600.

It is contemplated that in some embodiments, the manufacture by the manufacturing apparatus 230 of the computer system 200 (and/or of a remote/external computer system) may be performed by an additive manufacturing technique. For example, as mentioned above, the manufacturing apparatus 230 may be a 3D printing apparatus and, hence, may 3D print the given tooth-specific platform based on the data representative of the 3D-platform representation 1600.

It is also contemplated that in other embodiments, the manufacture of the given tooth-specific platform may be performed by the manufacturing apparatus employing other techniques such as, but not limited to, a melting technique.

As mentioned above, in some embodiments, the processor 150 may be configured to generate the 3D-bracket representation 3000 (see FIG. 30) of the given tooth-specific bracket to be to be attached to the specific tooth via the given tooth-specific platform. In such a case, it is contemplated that the processor 150 may be configured to trigger manufacture of the given tooth-specific platform and of the given tooth-specific bracket based on the 3D-platform representation 1600 and on the 3D-bracket representation 3000.

It is contemplated that the processor 150 may transmit to the manufacturing apparatus 230 (see FIG. 2) data representative of the 3D-platform representation 1600, data representative of the 3D-bracket representation 3000 and computer-readable instructions for triggering the manufacture of the given tooth-specific platform and of the given tooth-specific bracket.

In some embodiments, the processor 150 may trigger the manufacturing apparatus 230 to fabricate the given tooth-specific platform and the given tooth-specific bracket separately from one another.

In other embodiments however, the processor 150 may trigger the manufacturing apparatus 230 to integrally fabricate the given tooth-specific platform and the given tooth-specific bracket. For example, the given tooth-specific platform and the given tooth-specific bracket may be integrally fabricated by an additive manufacturing technique (and/or by other manufacturing techniques mentioned above).

In some embodiments of the present technology, the computer system 200 (the processor 150 thereof) may be configured to perform a method 1700 for generating a 3D representation of a given tooth-specific platform.

STEP 1702: Acquiring a 3D-Tooth Representation of the Tooth

The method 1700 begins at step 1702 with the processor 150 configured to acquire the 3D-tooth representation 700 (depicted in FIG. 7) of the specific tooth to which the given tooth-specific platform is to be attached.

As illustrated in FIG. 7, the 3D-tooth representation 700 has the surface 701 and has been generated based on the specific tooth of the patient to which the given tooth-specific platform is to be attached. For example, the 3D-tooth representation 700 may be acquired from the imaging device 220 of the computer system 200.

STEP 1704: Defining an Attachment Zone on the Surface of the 3D-Tooth Representation The method 1700 continues to step 1704 with the processor 150 configured to define the attachment zone 750 on the surface 701 of the 3D-tooth representation 700 (see FIG. 7). As described above, the attachment zone 750 has the zone perimeter 760 enclosing the surface portion of the 3D-tooth representation 700 corresponding to the surface portion of the specific tooth to which the tooth-specific platform is to be attached.

In some embodiments of the present technology, the processor 150 executing the step 1704 may be configured to define the attachment point 780 on the surface 701 of the 3D-tooth representation 700, and may use this attachment point 780 for defining the zone perimeter 760 of the attachment zone 750, such that the attachment point 780 is enclosed by the zone perimeter 760 of the attachment zone 750.

In other embodiments, the processor 150 may be configured to determine the minimum area (the minimum area may also be an input from a skilled professional) for attaching the given tooth-specific platform on the specific tooth. The processor 150 may also be configured to define the zone perimeter 760 of the attachment zone 750 around the attachment point 780 such that the zone perimeter 760 encloses the surface portion having at least the minimum area.

STEP 1706: Generating the 3D-Platform Representation

The method 1700 continues to step 1706 with the processor 150 configured to generate the 3D-platform representation 1600 depicted in FIG. 16 having (i) the tooth-oriented surface 1302, (ii) the perimeter wall 1604, and (iii) a tooth-opposite surface 1602.

It is contemplated that the tooth-oriented surface 1302 matches/conforms to the surface portion of the 3D-tooth representation 700 that corresponds to the surface portion of the specific tooth to which the given tooth-specific platform is to be attached and has the perimeter 1301 that matches/conforms to the zone perimeter 760. The perimeter wall 1604 extends (i) between the tooth-oriented surface 1302 and the tooth-opposite surface 1602 and (ii) away from the surface portion. It should be noted that the perimeter wall 1604 has the thickness 1606. The tooth-opposite surface 1602 matches/conforms to the expanded surface portion of the 3D-tooth representation 700 (such as the surface portion 1570 of the expanded 3D-tooth representation 1400 of FIG. 15).

It is contemplated that the tooth-oriented surface 1302 does not match/conform to the tooth-opposite surface 1602. Also, the expanded surface portion of the 3D-tooth representation 700, such as the surface portion 1570 of the expanded 3D-tooth representation 1400 of FIG. 15, does not match/conform to the surface portion of the 3D-tooth representation 700 enclosed by the zone perimeter 760.

In some embodiments of the present technology, the processor 150 may execute the step 1706 by first generating the intermediary 3D object (e.g., the preliminary 3D-platform representation 1300 depicted in FIG. 13) and, then, by generating the 3D-platform representation 1600 (see FIG. 16) from the intermediary 3D object.

In order to generate the intermediary 3D object, the processor 150 may be configured to acquire the print object 800 (see FIG. 8) and project it onto the surface 701 of the 3D-12863668.2 tooth representation 700. The processor 150 is thereby configured to define the projected object 900 (see FIG. 9) matching at least a portion of the surface 701 of the 3D-tooth representation 700. For example, the processor 150 may be configured to perform the projection operation 850 on the print object 800 such that the projected object 900 covers the totality of the attachment zone 750.

The processor 150 may then be configured to use the zone perimeter 760 for cutting the projected object 900. The processor 150 is thereby configured to define the tooth-oriented surface 1302 of the 3D-platform representation 1600. For example, the processor 150 may be configured to perform the cutting operation 1050 (one or more boolean operations) such that the tooth-oriented surface 1302 matches/conforms to the surface portion of the 3D-tooth representation 700 (and/or to the attachment zone 750) and such that it has the perimeter 1301 that matches/conforms to the zone perimeter 760.

The processor 150 may then be configured to extrude the tooth-oriented surface 1302 into the pre-determined direction (see FIGS. 12 and 13). The processor 150 is thereby configured to define the preliminary 3D-platform representation 1300 (the intermediary 3D object). For example, the processor 150 may be configured to perform the extrusion operation 1250 such that the preliminary 3D-platform representation 1300 resulting therefrom has (i) the tooth-oriented surface 1302, (ii) the preliminary perimeter wall 1306, and (iii) the another outer surface 1304.

As previously alluded to, in order to execute the step 1706, the processor 150 may also be configured to generate the 3D-platform representation 1600 from the preliminary 3D-platform representation 1300.

It is contemplated that the processor 150 may be configured to expand the 3D-tooth representation 700 by the pre-determined distance. The processor 150 is thereby configured to generate the expanded 3D-tooth representation 1400 depicted in FIG. 14 having an expanded surface 1401. For example, the processor 150 may be configured to perform the expansion operation 1450 on the 3D-tooth representation 700 by using a value of the thickness 1606 (which is may be a desired thickness of the given tooth-specific platform).

The processor 150 may then use the expanded surface 1401 for cutting the preliminary 3D-platform representation 1300 along the preliminary perimeter wall 1306. The processor 150 is thereby configured to define the perimeter wall 1604 and the tooth-opposite surface 1602 of the 3D-platform representation 1600. For example, the processor 150 may be configured to perform another cutting operation such that the expanded surface portion 1570 is used as a cutting trajectory for cutting the preliminary 3D-platform representation 1300 along the preliminary perimeter wall 1306.

In some embodiments, the processor 150 may also be configured to trigger manufacture of the given tooth-specific platform based on data representative of the 3D-platform representation 1660. As mentioned above, the fabrication may be performed by the manufacturing apparatus 230 by employing a variety of techniques such as, but not limited to: an additive manufacturing technique, a melting technique, and the like.

It is also contemplated that the processor 150 may also be configured to trigger manufacture of the given tooth-specific platform separately from or integrally with the dental appliance (e.g., the given tooth-specific bracket) that is to be attached to the specific tooth via the given tooth-specific platform.

Figure 31:
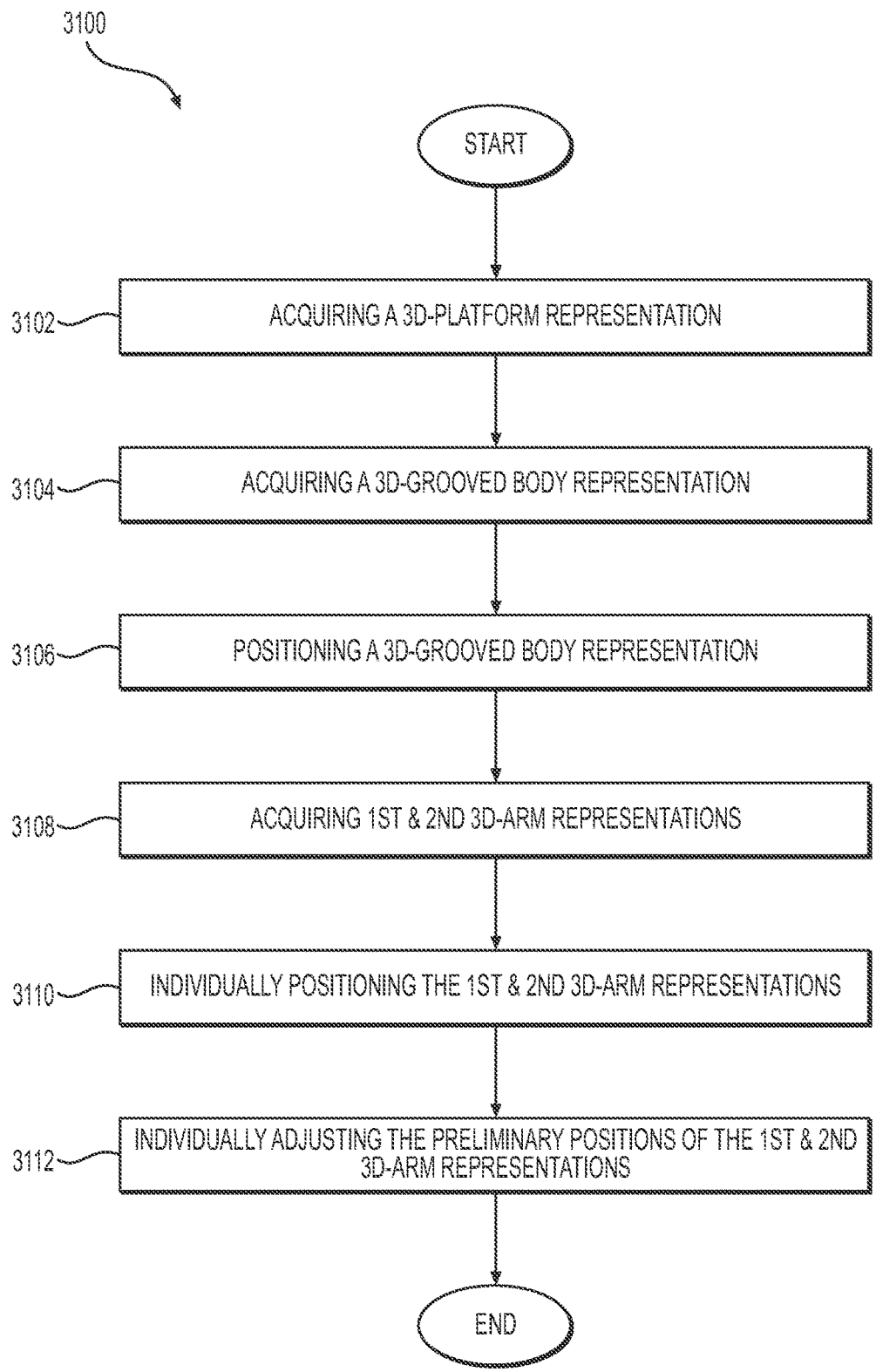
FIG. 31 is a schematic illustration of a method of generating the 3D-bracket representation executable by the processor of FIG. 1 in accordance with at least some embodiments of the present technology.

In some embodiments of the present technology, the computer system 200 may be configured to performed a method 3100 depicted in FIG. 31 for generating a given 3D-bracket representation, such as the 3D-bracket representation 3000, of a given tooth-specific bracket.

STEP 3102: Acquiring a 3D-Platform Representation of a Platform

The method begins at step 3102 with the processor 150 configured to acquire the 3D-platform representation 1900 depicted in FIG. 19. For example, the processor 150 may acquire the 3D-platform representation 1900 from the library. In another example, the processor 150 may be configured to generate the 3D-platform representation 1900 similarly to how the 3D-platform representation 1600 of FIG. 16 is generated.

STEP 3104: Acquiring a 3D-Grooved Body Representation of the Grooved Body

The method 3100 continues to step 3104 with the processor being configured to acquire a given 3D-grooved body representation of the grooved body of the given tooth-specific bracket. In some embodiments, the processor 150 may be configured to acquire the 3D-grooved body representation 3020 from the library. In other embodiments, the processor 150 may be configured to acquire the 3D-body structure representation 1802 and the 3D-groove structure representation 1804 from the library.

STEP 3106: Positioning the 3D-Grooved Body Representation Relative to the 3D-Platform Representation As depicted in FIG. 25, the processor 150 first positions 3D-grooved body representation 3020 relative to the 3D-platform representation 1900.

STEP 3108: Acquiring a First 3D-Arm Representation of a First Holding Arm and a Second 3D-Arm Representation of a Second Holding Arm With continued reference to FIG. 25, the processor 150 acquires a first 3D-arm representation 1806 and a second 3D-arm representation 1808. As part of step 3108, the processor 150 can further generate the ghost arms 2306, 2308 and the associated pairs of platform anchor points 2402, 2404, 2412, and 2414.

STEP 3110: Individually Positioning the First and the Second 3D-Arm Representations Relative to the 3D-Platform Representation Using the Respective Pairs of Platform Anchor Points With continued reference to FIG. 25, the processor 150 executes individually positioning the first and the second 3D-arm representations 1806, 1808 relative to the 3D-platform representation 1900 using the respective pairs of platform anchor points. This can be thought of a first stage or "course" positioning of the first and the second 3D-arm representations 1806, 1808 relative to the 3D-platform representation 1900.

More specifically, FIG. 25 illustrates a result of the individually positioning, by the processor 150, the first 3D-arm representation 1806 and the second 3D-arm representation 1808 relative (together with the associated ghost arms 2306, 2308) relative to the 3D-platform representation using the respective pairs of platform anchor points 2402, 2404, 2412, and 2414 thereby defining (i) a preliminary position of the first 3D-arm representation 1806 and (ii) a preliminary position of the second 3D-arm representation 1808.

STEP 3112: Individually Adjusting the Respective Preliminary Positions of the First and Second 3D-Arm Representations Relative to the 3D-Grooved Body Representation Using the Respective Adjustment Anchor Points At step 3112 and with continued reference to FIGS. 25 to 28, the processor 150 executes individually adjusting the respective preliminary positions of the first and second 3D-arm representations 1806, 1808 relative to the 3D-grooved body representation 3020 using the respective adjustment anchor points 2402, 2404, 2412, and 2414.

As has been alluded to above, FIGS. 25-29 further depict various stages of the process of individually adjusting, by the processor 150, the respective preliminary position of the first 3D-arm representation 1806 and of the second 3D-arm representation 1808 relative to the 3D-grooved body representation using the respective adjustment anchor points 2402, 2404, 2412, and 2414.

More specifically, FIG. 25 depicts a first adjustment 2550 away from the surface of the of the 3D-platform representation 1900 due to the penetration between the second 3D-arm representation 1808 and the 3D-platform representation 1900. FIG. 26 depicts a result of such the first adjustment 2550.

FIG. 27 depicts a second adjustment 2750 of the first 3D-arm representation 1806 towards the 3D-platform representation 1900 and FIG. 28 depicts a result 1906 of such the second adjustment 2750.

Even though not depicted, further adjustments may be required, for example, to the first 3D-arm representation 1806 away from the 3D-platform representation 1900.

FIG. 29 depicts schematically a first direction of adjustment 2902 of the first 3D-arm representation 1806 towards the 3D-platform representation 1900 and a second direction of adjustment 2904 of the second 3D-arm representation 1808.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method of generating a 3D-platform representation of a tooth-specific platform for attachment of a dental appliance to a tooth of a patient, the method executable by a processor, the method comprising:
    acquiring, by the processor, a 3D-tooth representation of the tooth,
        the 3D-tooth representation having a surface and having been generated based on the tooth of the patient;
    defining, by the processor, an attachment zone on the surface of the 3D-tooth representation,
        the attachment zone having a zone perimeter enclosing a surface portion of the 3D-tooth representation corresponding to a surface portion of the tooth to which the tooth-specific platform is to be attached;
    generating, by the processor, the 3D-platform representation having (i) a tooth-oriented surface, (ii) a perimeter wall, and (iii) a tooth-opposite surface,
        the generating comprising:
            generating, by the processor, a preliminary 3D-platform representation; and
            generating, by the processor, the 3D-platform representation from the preliminary 3D-platform representation by:
                expanding, by the processor, the 3D-tooth representation by a pre-determined distance, thereby generating an expanded 3D-tooth representation having an expanded surface;
                using, by the processor, the expanded surface for cutting the preliminary 3D-platform representation along the preliminary perimeter wall, thereby defining (i) the perimeter wall and (ii) the tooth-opposite surface of the 3D-platform representation;
            the tooth-oriented surface matching the surface portion of the 3D-tooth representation and having a perimeter matching the zone perimeter,
            the perimeter wall extending (i) between the tooth-oriented surface and the tooth-opposite surface and (ii) away from the surface portion, and
            the tooth-opposite surface matching the expanded surface portion of the expanded 3D-tooth representation.

2. The method of claim 1, wherein the expanded surface portion does not match the surface portion.

3. The method of claim 1, wherein the defining the attachment zone comprises:
    defining, by the processor, an attachment point on the surface of the 3D-tooth representation; and
    using, by the processor, the attachment point for defining the zone perimeter of the attachment zone,
        the attachment point being enclosed by the zone perimeter of the attachment zone.

4. The method of claim 3, wherein the using the attachment point for defining the zone perimeter of the attachment zone comprises:
    determining, by the processor, a minimum area for attaching the tooth-specific platform on the tooth; and
    defining, by the processor, the zone perimeter of the attachment zone around the attachment point such that the zone perimeter encloses the surface portion having at least the minimum area.

5. The method of claim 1, wherein the generating the preliminary 3D-platform representation comprises:
    projecting, by the processor, a print object onto the surface of the 3D-tooth representation,
        thereby defining a projected object matching at least a portion of the surface of the 3D-tooth representation:
    using, by the processor, the zone perimeter for cutting the projected object, thereby defining the tooth-oriented surface of the 3D-platform representation,
    the tooth-oriented surface matching the surface portion of the 3D-tooth representation and having a perimeter matching the zone perimeter:
    extruding, by the processor, the tooth-oriented surface into a pre-determined direction, thereby defining the preliminary 3D-platform representation having (i) the tooth-oriented surface, (ii) a preliminary perimeter wall, and (iii) another surface.

6. The method of claim 5, wherein the print object has a grid-type relief.

7. The method of claim 1, wherein the method further comprises:
    triggering, by the processor, manufacture of the tooth-specific platform based on the 3D-platform representation.

8. The method of claim 7, wherein the manufacture is performed by an additive manufacturing technique.

9. The method of claim 7, wherein the manufacture is performed by a melting technique.

10. The method of claim 1, wherein the method further comprises:
    generating, by the processor, a 3D-bracket representation of a bracket to be to be attached to the tooth, the bracket being the dental appliance.

11. The method of claim 10, wherein the method further comprises:
    triggering, by the processor, manufacture of the tooth-specific platform and of the bracket based on the 3D-platform representation and on the 3D-bracket representation.

12. The method of claim 11, wherein the tooth-specific platform and the bracket are integrally fabricated.

13. The method of claim 12, wherein the tooth-specific platform and the bracket are integrally fabricated by an additive manufacturing technique.

14. A processor for generating a 3D-platform representation of a tooth-specific platform for attachment of a dental appliance to a tooth of a patient, the processor being configured to:
acquire a 3D-tooth representation of the tooth,
the 3D-tooth representation having a surface and having been generated based on the tooth of the patient;
define an attachment zone on the surface of the 3D-tooth representation,
the attachment zone having a zone perimeter enclosing a surface portion of the 3D-tooth representation corresponding to a surface portion of the tooth to which the tooth-specific platform is to be attached;
generate the 3D-platform representation having (i) a tooth-oriented surface, (ii) a perimeter wall, and (iii) a tooth-opposite surface, by:
generating a preliminary 3D-platform representation; and
generating the 3D-platform representation from the preliminary 3D-platform representation by:
expanding the 3D-tooth representation by a predetermined distance, thereby generating an expanded 3D-tooth representation having an expanded surface;
using the expanded surface for cutting the preliminary 3D-platform representation along the preliminary perimeter wall, thereby defining (i) the perimeter wall and (ii) the tooth-opposite surface of the 3D-platform representation;
the tooth-oriented surface matching the surface portion of the 3D-tooth representation and having a perimeter matching the zone perimeter,
the perimeter wall extending (i) between the tooth-oriented surface and the tooth-opposite surface and (ii) away from the surface portion, and
the tooth-opposite surface matching the expanded surface portion of the expanded 3D-tooth representation.

15. The processor of claim 14, wherein the expanded surface portion does not match the surface portion.

16. The processor of claim 14, wherein the processor configured to define the attachment zone comprises the processor being configured to:
define an attachment point on the surface of the 3D-tooth representation; and
use the attachment point for defining the zone perimeter of the attachment zone,
the attachment point being enclosed by the zone perimeter of the attachment zone.

17. The processor of claim 16, wherein the processor configured to use the attachment point for defining the zone perimeter of the attachment zone comprises the processor being configured to:
determine a minimum area for attaching the tooth-specific platform on the tooth; and
define the zone perimeter of the attachment zone around the attachment point such that the zone perimeter encloses the surface portion having at least the minimum area.

18. The processor of claim 14, wherein the processor configured to generate the 3D-platform representation comprises the processor being configured to:
generate a preliminary 3D-platform representation; and
generate the 3D-platform representation from the preliminary 3D-platform representation.

* * * * *